United States Patent
Brennan et al.

(10) Patent No.: US 11,549,945 B2
(45) Date of Patent: Jan. 10, 2023

(54) DNAZYME-BASED SENSOR FOR HELICOBACTER PYLORI

(71) Applicant: McMaster University, Hamilton (CA)

(72) Inventors: John D. Brennan, Dundas (CA); Yingfu Li, Dundas (CA); Monsur Ali, Hamilton (CA); Carlos Filipe, Ancaster (CA); Michael Gregory Wolfe, Ancaster (CA)

(73) Assignee: McMaster University, Hamilton (CA)

( * ) Notice: Subject to any disclaimer, the term of this patent is extended or adjusted under 35 U.S.C. 154(b) by 320 days.

(21) Appl. No.: 16/875,707

(22) Filed: May 15, 2020

(65) Prior Publication Data
US 2020/0363413 A1 Nov. 19, 2020

Related U.S. Application Data

(60) Provisional application No. 62/848,240, filed on May 15, 2019.

(51) Int. Cl.
*C12Q 1/6816* (2018.01)
*G01N 33/569* (2006.01)
*G01N 33/543* (2006.01)

(52) U.S. Cl.
CPC . *G01N 33/56922* (2013.01); *G01N 33/54393* (2013.01); *G01N 2333/98* (2013.01)

(58) Field of Classification Search
None
See application file for complete search history.

(56) References Cited

PUBLICATIONS

Fonkwo. Pricing infectious disease. The economic and health implications of infectious diseases. EMBO Reports, vol. 9, Special Issue, published Jul. 2008, pp. S13-S17.
Suhrcke et al. The Impact of Economic Crises on Communicable Disease Transmission and Control: A Systematic Review of the Evidence PLoS One, vol. 6(6), e20724, published Jun. 10, 2011, pp. 1-12.
Uemura et al. Helicobacter pylori infection and the development of gastric cancer. The New England Journal of Medicine, vol. 345(11), published Sep. 13, 2001, pp. 784-789.
Khatoon et al. Role of Helicobacter pylori in gastric cancer: Updates. World Journal of Gastrointestinal Oncology, vol. 8(2), published Feb. 15, 2016, pp. 147-158.
Calvet. Diagnosis of Helicobacter pylori Infection in the Proton Pump Inhibitor Era. Gastroenterology Clinics, vol. 44 (3), published Sep. 1, 2015, pp. 507-518.
De Falco et al. Molecular Mechanisms of Helicobacter pylori Pathogenesis. Journal of Cellular Physiology, vol. 230 (8), published Aug. 2015, pp. 1702-1707.
Jiang et al. Population attributable burden of Helicobacter pylori-related gastric cancer, coronary heart disease, and schemic stroke in China. European Journal of Clinical Microbiology & Infectious Diseases, vol. 36, published online Oct. 22, 2016, pp. 199-212.
Talebi Bezmin Abadi. Helicobacter pylori: emergence of a Superbug. Frontiers in Medicine, vol. 1(34), published Oct. 14, 2014, pp. 1-2.
Ghotaslou et al. Prevalence of antibiotic resistance in Helicobacter pylori: A recent literature review. World Journal of Methodology, vol. 5(3), published Sep. 26, 2015, pp. 164-174.
Backert et al. Pathogenesis of Helicobacter pylori infection. Helicobacter, vol. 21(Suppl. 1), published Sep. 2016, pp. 19-25.
Ferwana et al. Accuracy of urea breath test in Helicobacter pylori infection: Meta-analysis. World Journal of Gastroenterology: WJG, vol. 21(4), published Jan. 28, 2015, pp. 1305-1314.
Carlini and Ligabue-Braun. Ureases as multifunctional toxic proteins: A review. Toxicon, vol. 110, published Feb. 1, 2016, pp. 90-109.
Boutal et al. Development and Validation of a Lateral Flow Immunoassay for Rapid Detection of NDM-Producing Enterobacteriaceae. Journal of Clinical Microbiology, vol. 55(7), published Jul. 2017, pp. 2018-2029.
Scharinger et al. Multiplexed Lateral Flow Test for Detection and Differentiation of Cronobacter sakazakii Serotypes O1 and O2 Frontiers in Microbiology, vol. 8, 1826, published Sep. 20, 2017, pp. 1-13.
Ali et al. Fluorogenic DNAzyme Probes as Bacterial Indicators. Angewandte Chemie International Edition, vol. 50, first published Mar. 15, 2011, pp. 3751-3754.
Shen et al. A Catalytic DNA Activated by a Specific Strain of Bacterial Pathogen. Angewandte Chemie International Edition, vol. 55(7), published Feb. 12, 2016, pp. 2431-2434.
Aguirre et al. A Sensitive DNA Enzyme-Based Fluorescent Assay for Bacterial Detection. Biomolecules, vol. 3(3), published Sep. 2013, pp. 563-577.
Ali et al. A Printed Multicomponent Paper Sensor for Bacterial Detection. Scientific Reports, vol. 7(1), 12335, published Sep. 26, 2017, pp. 1-10.
Tram et al. Translating Bacterial Detection by DNAzymes into a Litmus Test. Angewandte Chemie International Edition, vol. 53, first published Sep. 11, 2014, pp. 12799-12802.
Mazumdar et al. Easy-to-use dipstick tests for detection of lead in paints using non-cross-linked gold nanoparticle-DNAzyme conjugates. Chemical Communications, vol. 46(9), first published Jan. 26, 2010, pp. 1416-1418.
Fang et al. Lateral flow nucleic acid biosensor for Cu2+ detection in aqueous solution with high sensitivity and selectivity. Chemical Communications, vol. 46(47), published online Nov. 4, 2010, pp. 9043-9045.

(Continued)

*Primary Examiner* — Christopher M Gross
(74) *Attorney, Agent, or Firm* — Melanie Szweras; Herman Cheung; Bereskin & Parr LLP/S.E.N.C.R.L., s.r.l.

(57) ABSTRACT

Provided herein are nucleic acid-cleaving catalytic nucleic acid probes, biosensors and lateral flow biosensor devices and methods and kits of using the probes, biosensors and lateral flow biosensor devices for detecting an analyte present on or generated from a microorganism in a test sample, including *Helicobacter pylori* and methods for determining whether a subject has a *Helicobacter pylori* infection.

17 Claims, 15 Drawing Sheets
Specification includes a Sequence Listing.

(56) References Cited

PUBLICATIONS

Liu et al. A Simple and Sensitive "Dipstick" Test in Serum Based on Lateral Flow Separation of Aptamer-Linked Nanostructures. Angewandte Chemie International Edition, vol. 45(47), first published Nov. 27, 2006, pp. 7955-7959.

Cannistraro and Kennell. Purification and characterization of ribonuclease M and mRNA degradation in *Escherichia coli*. European Journal of Biochemistry, vol. 181(2), published May 1989, pp. 363-370.

Vogelstein and Gillespie. Preparative and analytical purification of DNA from agarose. Proceedings of the National Academy of Sciences, vol. 76(2), published Feb. 1, 1979, pp. 615-619.

Zheng et al. Affinity binding of aptamers to agarose with DNA tetrahedron for removal of hepatitis B virus surface antigen. Colloids and Surfaces B: Biointerfaces, vol. 178, published Jun. 1, 2019, pp. 80-86.

Jahanshahi-Anbuhi et al. Pullulan Encapsulation of Labile Biomolecules to Give Stable Bioassay Tablets. Angewandte Chemie International Edition, vol. 53(24), first published Apr. 24, 2014, pp. 6155-6158.

Hsieh et al. RNA Protection is Effectively Achieved by Pullulan Film Formation. ChemBioChem, vol. 18(6), published Mar. 16, 2017, pp. 502-505.

Liu et al. Target-Induced and Equipment-Free DNA Amplification with a Simple Paper Device. Angewandte Chemie International Edition, vol. 55(8), first published Jan. 8, 2016, pp. 2709-2713.

Konieczna et al. Bacterial Urease and its Role in Long-Lasting Human Diseases. Current Protein and Peptide Science, vol. 13(8), published Dec. 1, 2012, pp. 789-806.

Mora and Arioli. Microbial Urease in Health and Disease. PLoS Pathogens, vol. 10(12):e1004472, published Dec. 11, 2014, pp. 1-4.

Bradbury et al. Urease production as a marker of virulence in Pseudomonas aeruginosa. British Journal of Biomedical Science, vol. 71(4), published Jan. 1, 2014, pp. 175-177.

Makristathis et al. Detection of Helicobacter pylori in Stool Specimens by PCR and Antigen Enzyme Immunoassay. Journal of Clinical Microbiology, vol. 36(9), published Sep. 1, 1998, pp. 2772-2774.

FIG. 1a
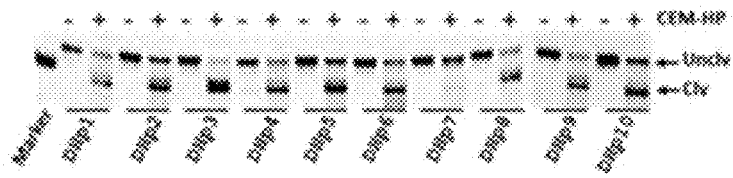
FIG. 1b
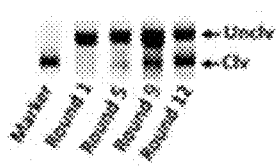
FIG. 1c
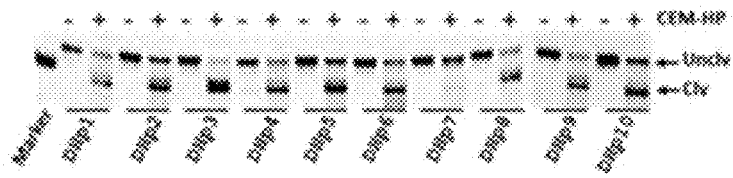
FIG. 1d
FIG. 1e
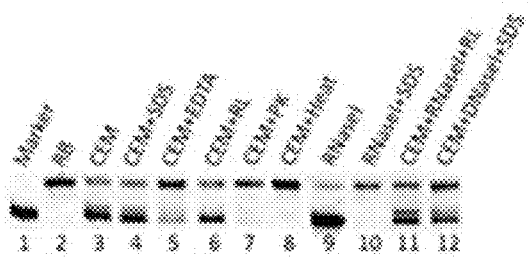
FIG. 1f
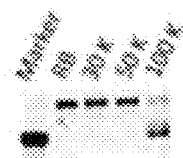
FIG. 1g
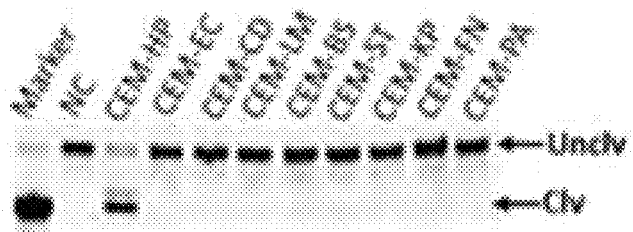

```
DL:  5'-ATGCCATCCTACCAAC-N50-GAGCTCTGAACTCG-3'
FP:  5'-ATGCCATCCTACCAAC-3'
RP1: 5'-CGAGTTCAGAGCTC-3'
RP2: 5'-A20-L-CGAGTTCAGAGCTC-3'
FS:  5'-CTATGAACTGACQRFGACCTCACTACCAAG-3'
LT:  5'-GTTGGTAGGATGGCATCTTGGTAGTGAGGTC-3'
```

FIG. 6a

```
           ATGCCATCCTACCAACCCATGTGGTTTGTTGAGATGGTCTTTGGTATGTGCGGTCCGAGGGTAGAGCTCTGAACTCG
DHp3T1:
           ATGCCATCCTACCAACCCATGTGGTTTGTTGAGATGGTCTTTGGTATGTGCGGTCCGAGGGTA~~~~~~~~~~~~~~~
DHp3T2:
           ~~~~~~~~~~~~~~~CCATGTGGTTTGTTGAGATGGTCTTTGGTATGTGCGGTCCGAGGGTAGAGCTCTGAACTCG
DHp3T3:
           ~~~~~~~~~~~~~~~CCATGTGGTTTGTTGAGATGGTCTTTGGTATGTGCGGTCCGAGGGTA~~~~~~~~~~~~~~~
DHp3T4:
           ATGCCATC~~~~~~~~~~~~~~~~~~~~~~~GATGGTCTTTGGTATGTGCGGTCCGAGGGTAGAGCTCTGAACTCG
DHp3T4M:
           ATGCCATC~~~~~~~~~~~~~~~~~~~~~~~GATGGTCTTTGGTATGTGCGGTCgacgGGTAGAGCTCTGAACTCG
```

FIG. 6b

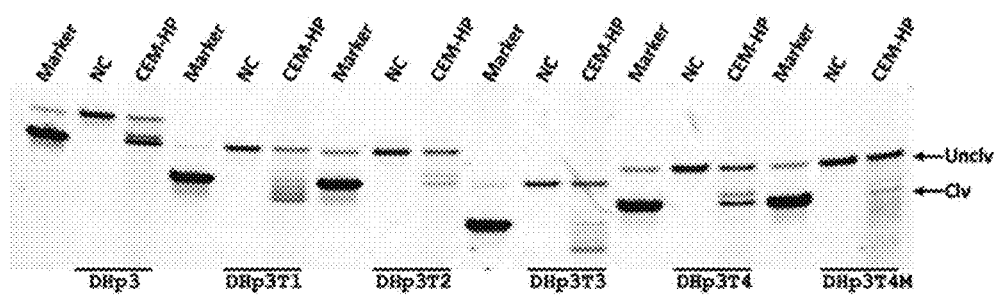

DNAZYME-BASED SENSOR FOR HELICOBACTER PYLORI

CROSS REFERENCE TO RELATED APPLICATION

The present disclosure claims priority from U.S. provisional application No. 62/848,240 filed on May 15, 2019, which is hereby incorporated by reference in its entirety.

INCORPORATION OF SEQUENCE LISTING

A computer readable form of the Sequence Listing "3244-P59092US01_RevisedSequenceListing.txt" (16,226 bytes), submitted via EFS-WEB and updated on Jul. 30, 2020, is herein incorporated by reference.

FIELD

The present disclosure relates to biosensors for pathogenic bacteria, and in particular, a DNAzyme and paper-based biosensor for detecting *Helicobacter pylori*.

BACKGROUND

Infections by pathogenic bacteria are a major threat to public health as they cause many costly outbreaks around the world each year [1]. Among bacterial pathogens, *Helicobacter pylori* (HP) is particularly important, as more than 50% of the world population is infected by this pathogen [2]. HP is a gram-negative microaerophilic fastidious human pathogen that colonizes in the human stomach. HP is strongly related to gastric carcinoma and is responsible for ~80% of gastric ulcers and ~95% of duodenal ulcers [3]. Moreover, this pathogen has been considered as an emerging superbug due to increased reports of drug resistant strains of HP [4]. Therefore, accurate diagnosis of HP is critical to managing gastrointestinal health.

Several techniques have been developed for the detection of HP, which can be categorized into invasive and non-invasive tests [3c, 4a, 5]. Invasive tests include endoscopic biopsy-based histology, followed by a rapid urease test and molecular PCR. This diagnostic option is not suitable for routine applications due to high cost and long test time. Among the non-invasive tests, the Urea Breath Test (UBT) and the stool antigen test are commonly used. UBT relies on the production of urease by HP in the stomach. A solution of urea labeled with $^{13}C$ (or $^{14}C$) is ingested by the patient, and the urease produced by HP in the stomach hydrolyses the isotopically labeled urea to generate $^{13}CO_2$ (or $^{14}CO_2$) in exhaled breath, which can be collected and analyzed using analytical instrumentation. Although the test is noninvasive and quite sensitive, the results are not always reliable as there are other bacteria that produce urease as well [6]. The stool antigen based biochemical tests, such as the antibody based lateral flow device (LFD) and dipstick tests, although simple enough for point-of-care applications, suffer from poor specificity and sensitivity, with a limit of detection of ~$10^7$ cfu/mL [7]. Reliable detection of pathogenic bacteria in complex biological samples using simple assays or devices remains a major challenge. Therefore, there is still a significant demand for simple HP tests that are more sensitive and accurate.

SUMMARY

The present inventors have provided a simple colorimetric paper biosensor device capable of providing specific and sensitive detection of *Helicobacter pylori* (*H. pylori*), a pathogen strongly linked to gastric carcinoma, gastric ulcers and duodenal ulcers, in stool samples. The sensor molecule, an RNA-cleaving DNAzyme derived by in vitro selection, is activated by a protein biomarker from *H. pylori*. The colorimetric paper biosensor device, designed on the basis of the RNA-cleaving property of the DNAzyme, is capable of delivering sensitive detection of *H. pylori* in human stool samples with minimal sample processing, and provides results in minutes. It remains fully functional under storage at ambient temperature for at least 130 days. This work lays a foundation for developing DNAzyme-enabled paper biosensor devices as point-of-care diagnostics for monitoring pathogens in complex samples. The disclosure also relates to a method of detecting a microorganism in a sample using a biosensor device, and kits for detecting a microorganism comprising a biosensor device.

In accordance with a broad aspect of the present disclosure, there is provided a lateral flow biosensor device for detecting the presence of an analyte in a test sample, comprising:
  i) a buffer zone for applying a running buffer, the buffer zone being connected through a flow channel to ii) a sensor zone for applying a test sample comprising an immobilized biosensor entrapped by a stabilizing matrix, the sensor zone being connected through a flow channel to iii) a detection zone for indicating the presence or a range of levels of the analyte,
  wherein the immobilized biosensor in the sensor zone is immobilized to a solid support, and the immobilized biosensor comprises:
    a) a sensor nucleic acid molecule comprising a first region comprising a nucleic acid-cleaving catalytic nucleic acid probe specific to the analyte, and a second region comprising a nucleic acid sequence having a linkage substrate and a releasable tag nucleic acid molecule, and
    b) a reporter conjugated to the releasable tag nucleic acid molecule of the sensor nucleic acid molecule or an adapter nucleic acid molecule conjugated with a reporter,
  wherein the adapter nucleic acid molecule comprises a nucleic acid sequence complementary to the releasable tag nucleic acid molecule or a portion thereof, or sufficient complementarity that provides a strong enough interaction to prevent dehybridization,
  wherein the adapter nucleic acid molecule hybridizes to the releasable tag nucleic acid fragment to form a releasable fragment comprising the reporter,
  wherein, in the presence of analyte, the nucleic acid-cleaving catalytic nucleic acid probe is activated and cleaves the linkage substrate at a cleavage site, thereby releasing the releasable tag nucleic acid molecule conjugated with the reporter, or the releasable fragment comprising the reporter, and
  wherein, upon cleavage, the releasable tag nucleic acid molecule conjugated with the reporter, or the releasable fragment conjugated with the reporter migrates to the detection zone due to lateral flow of the running buffer to produce a signal.

In an embodiment, the reporter is a reporter enzyme or a gold nanoparticle. In an embodiment, the reporter is a reporter enzyme and the detection zone comprises a reporting solution entrapped by the stabilizing matrix. In an embodiment, the solid support comprises agarose beads, optionally the biosensor is immobilized to the agarose beads by biotin-streptavidin interaction. In an embodiment, the analyte is a protein. In an embodiment, the stabilizing matrix is oxygen impermeable, has a viscosity of between 10-50 centipoise, and provides stability to the immobilized biosensor in the sensor zone and the reporting solution in the detection zone for at least four months, optionally the stabilizing matrix comprises pullulan. In an embodiment, the lateral flow biosensor device comprises nitrocellulose paper, a polymer support layer and a hydrophobic material.

In an embodiment, the linkage substrate comprises a ribonucleotide linkage substrate. In an embodiment, the nucleic acid-cleaving catalytic nucleic acid probe comprises a DNAzyme. In an embodiment, the DNAzyme comprises a sequence of any one of SEQ ID NO: 1-14 or 28-36, or a functional fragment or modified derivative thereof. In an embodiment, the reporter enzyme is urease, alkaline phosphatase, cholinesterase, or horseradish peroxidase. In an embodiment, the reporter enzyme is urease and the reporting solution comprises urea and a pH sensitive dye, optionally phenol red, bromothymol blue, 6,8-dinitro-2,4-(1H)quinazolinedione, brilliant yellow, neutral red, m-nitrophenol, cresol red, naphtholphthalein, phenolphthalein, m-cresol purple, or o-cresolphthalein complexone. In an embodiment, the running buffer comprises acetic acid, optionally 1 mM acetic acid.

In an embodiment, the analyte comprises a molecule, compound or substance that is present in or on a microorganism, or is generated, excreted, secreted or metabolized by a microorganism. In an embodiment, wherein the microorganism is *Helicobacter pylori, Escherichia coli* O157:H7, *Clostridium difficile, Salmonella serovar typhimurium, Listeria monocytogenes, Klebsiella pneumoniae, Fusobacterium nucleatum, Pseudomonas aeruginosa, Bacteroides fragilis, Enterococcus faecium* or *Streptococcus salivarius*.

In another aspect, there is also provided a kit for detecting a microorganism, wherein the kit comprises the lateral flow biosensor device described herein in this disclosure, one or more components required thereof, and instructions for use of the kit for detecting the microorganism.

In another aspect, there is also provided a method of detecting a microorganism in a test sample, comprising:
applying the test sample to the sensor zone of the lateral flow biosensor device described herein in this disclosure,
wherein the test sample comprises an analyte from a microorganism, wherein the analyte contacts the immobilized biosensor in the sensor zone and activates the nucleic acid-cleaving nucleic acid probe which cleaves the linkage substrate at a cleavage site and releases a fragment comprising the reporter,
applying a running buffer to the buffer zone of the lateral flow biosensor device, whereby the running buffer laterally flows into the sensor zone and the released fragment comprising the reporter then moves laterally to the detection zone,
allowing the reporter to produce a signal, and
detecting the signal in the detection zone, optionally the signal is a color change signal, optionally color is indicative of amount of analyte.

In an embodiment, the reporter is a reporter enzyme or a gold nanoparticle, optionally the reporter enzyme is urease, alkaline phosphatase, cholinesterase, or horseradish peroxidase.

In another aspect, there is also provided a sensor nucleic acid molecule comprising a first region comprising a nucleic acid-cleaving catalytic nucleic acid probe having a sequence of any one of SEQ ID NO: 1-14 or 28-36, or a functional fragment or modified derivative thereof, and a second region comprising a nucleic acid sequence having a linkage substrate and a releasable tag nucleic acid molecule.

In another aspect, there also provided a biosensor for detecting *Helicobacter pylori* in a test sample, comprising:
i) a sensor nucleic acid molecule described herein in this disclosure attached to a solid support; and
ii) a reporter conjugated to the releasable tag nucleic acid molecule of the sensor nucleic acid molecule or an adapter nucleic acid molecule conjugated with a reporter,
wherein the adapter nucleic acid molecule comprises a nucleic acid sequence complementary to the releasable tag nucleic acid molecule or a portion thereof, or sufficient complementarity that provides a strong enough interaction to prevent dehybridization,
wherein the adapter nucleic acid molecule hybridizes to the releasable tag nucleic acid molecule to form a releasable fragment comprising the reporter,
wherein, in the presence of analyte, the nucleic acid-cleaving catalytic nucleic acid probe is activated and cleaves the linkage substrate, thereby releasing the releasable tag nucleic acid molecule conjugated with the reporter or the releasable fragment comprising the reporter available for detection or detection reaction, optionally the test sample is a stool sample.

In an embodiment, the solid support are agarose beads, wherein the reporter enzyme comprises urease, and wherein the detection comprises measuring color changes using urea and a pH sensitive dye, optionally phenol red, bromothymol blue, 6,8-dinitro-2,4-(1H)quinazolinedione, brilliant yellow, neutral red, m-nitrophenol, cresol red, naphtholphthalein, phenolphthalein, m-cresol purple, or o-cresolphthalein complexone, optionally color is indicative of amount of analyte.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

DRAWINGS

The embodiments of the disclosure will now be described in greater detail with reference to the attached drawings in which:

FIG. 1a shows the sequence of the DNA library used for the DNAzyme selection (written from 5'-3'). Q: dabcyl-dT, R: adenine ribonucleotide, F: Fluorescein-dT, N: random nucleotide.

FIG. 1b shows gel-based activity assessment of the DNA pools at the indicated selection rounds. 10% denaturing (7 M urea) polyacrylamide gel electrophoresis (10% dPAGE) was used to assess the cleavage activity. The marker lane contained the expected cleavage fragment (Clv), which moves faster than the uncleaved (Unclv) DNA pools.

FIG. 1c shows the results of cleavage test of the top 10 DNAzyme sequences.

FIG. 1d shows the sequence of DHp3T4, a shortened version of DHp3.

FIG. 1e shows the results of assessment of the nature of the target that activates DHp3T4. DHp3T4 was incubated with reaction buffer (RB without CEM) or CEM-HP treated with SDS, EDTA, ribolock (RL), heat denaturation (10 min at 90° C.), RNase I, and RNase I plus SDS, RNase I followed by addition of ribolock (RNase inhibitor), DNaseI followed by SDS to inhibit DNaseI.

FIG. 1f shows estimation of the molecular weight of the target. CEM-HP was passed through molecular weight sizing columns of 30K, 50K and 100K Daltons and the filtrate was then tested in the gel based assay. RB: reaction with 1× SB without CEM-HP.

FIG. 1g shows the results of a specificity test. DHp3T4 was tested with CEM prepared from various bacteria. HP: *H. pylori*, EC: *E. coli*, CD: *C. difficile*, LM: *L. monocytogenes*, BS: *B. subtilis*, ST: *S. typhimurium*, KP: *K pneumoniae*, FN: *F. nucleatum*, PA: *P. aeruginosa*.

Figure 2:
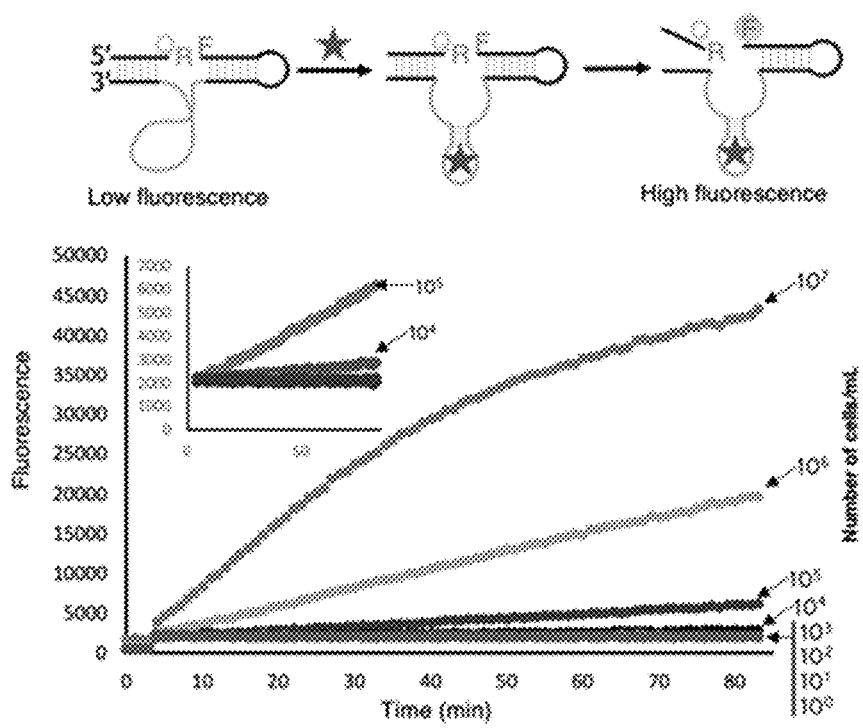

FIG. 2 shows fluorescence response of DHp3T4 to various concentrations of HP. The signaling reaction is shown at the top of the figure.

Figure 3A:
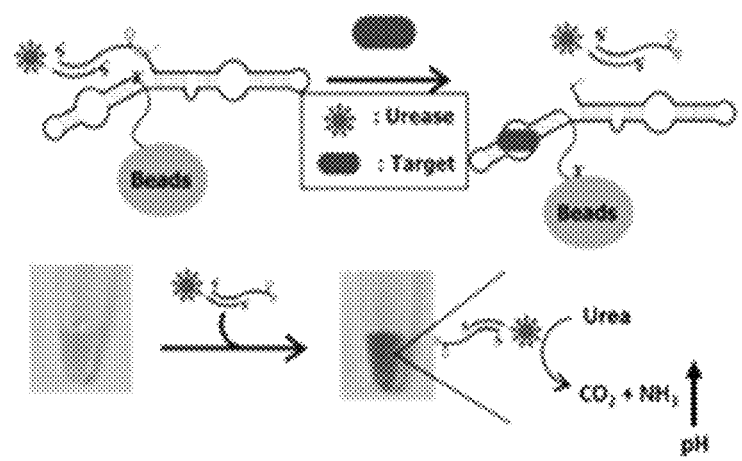

FIG. 3a shows the working principle of solution-based litmus test. The DNAzyme is immobilized on agarose beads through a streptavidin-biotin interaction. Urease is attached at the 5'-end of the DNAzyme through a sequence tag. Upon addition of a HP-containing test sample, the cleavage reaction frees the urease from the beads, which is collected and added into a reporting reaction containing urea and phenol red. The urease catalyzes hydrolysis of urea producing ammonia, which raises the pH and changes the color of the reporting solution from yellow to red.

Figure 3B:
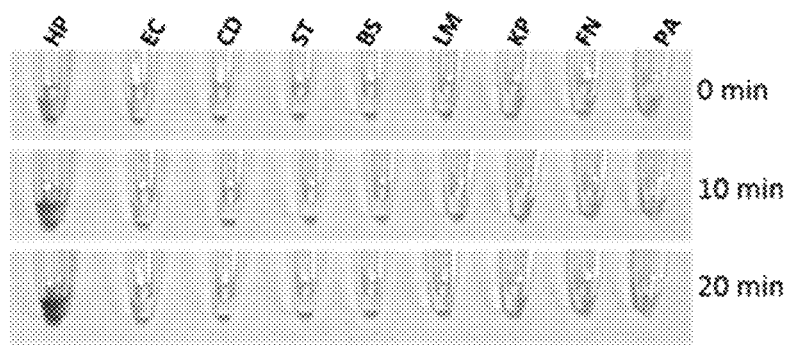

FIG. 3b shows the results of a selectivity test using stool samples spiked with various bacterial species. Bacteria are as noted in FIG. 1g.

Figure 3C:
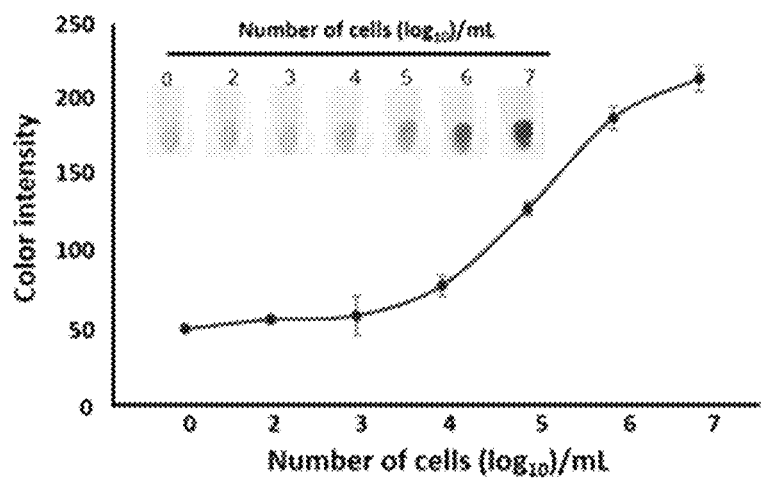

FIG. 3c shows limit of detection of HP in spiked human stool samples.

Figure 4A:
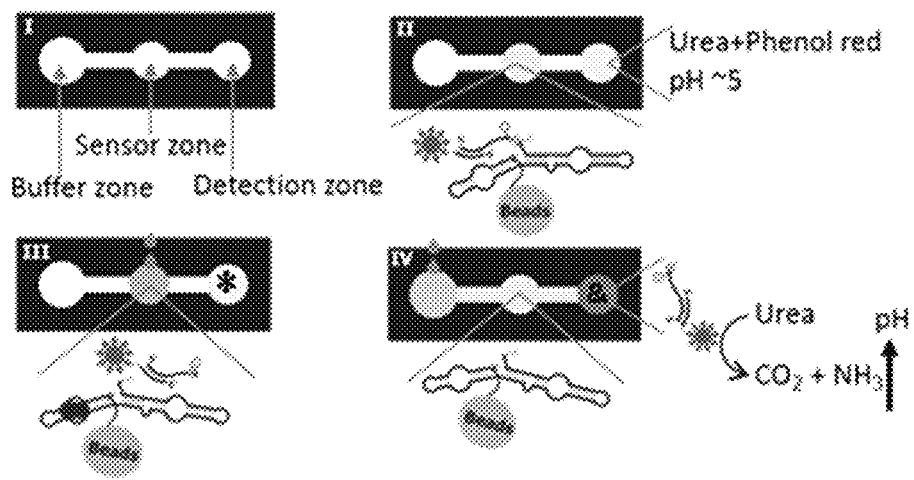

FIG. 4a is a schematic of a design of paper-based biosensor device. I) Layout of three zones. Black part indicates wax barrier and white portion is the device with different zones as noted. II) The sensor and reporting films are pasted in the middle sensor zone and the right detection zone, respectively. III) Sample is added on the sensor zone and allowed to react. IV) Running buffer is added on the buffer zone to move the freed urease molecules to the detection zone where they hydrolyze urea to produce ammonia and change the color from yellow (asterisk in III) to red (ampersand in IV).

Figure 4B:
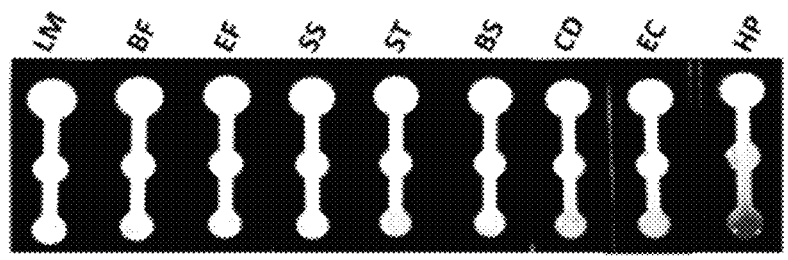

FIG. 4b shows selectivity of the sensor. Bacteria as noted in FIG. 2 except: BF: *Bacteroides fragilis*, EF: *Enterococcus faecium*, SS: *Streptococcus salivarius*.

Figure 4C:
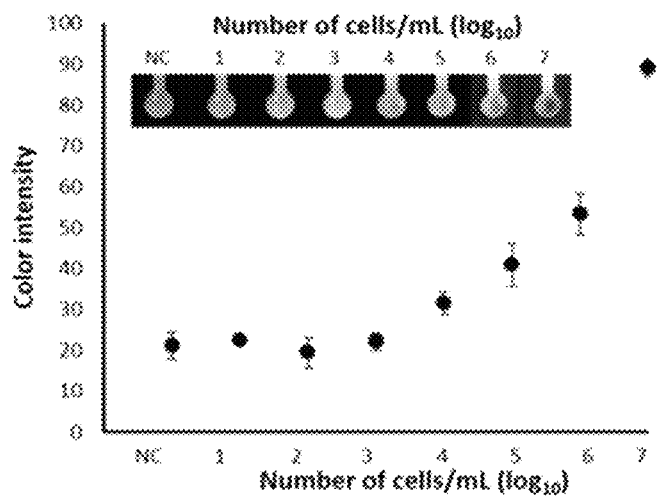

FIG. 4c shows detection limit for the *H. pylori* sensor.

Figures 5A, 5B:
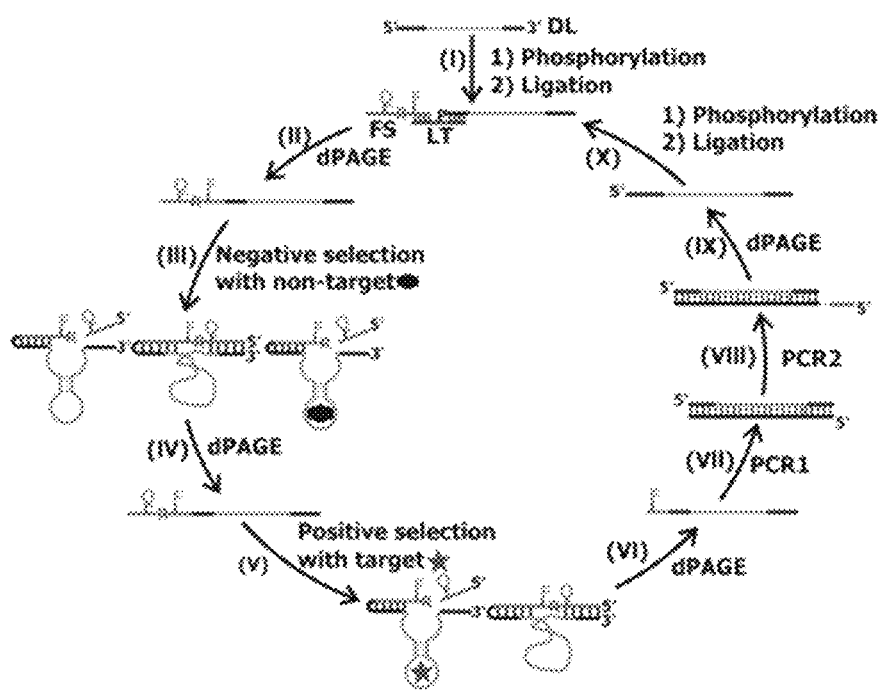

FIG. 5a shows the sequences of all the DNA molecules used for the HP-activated DNAzyme selection experiment. DL is the library with 50 central random nucleotides (N50) flanked by two constant sequence regions. FP, RP1 and RP2 are the forward and reverse primers for PCR, respectively. L in RP2 is a glycol linker with a poly-A tail that generates PCR products of asymmetric lengths for purification by dPAGE. FS is the fluorogenic DNA-RNA substrate: F is fluorescein-dT, R is riboadenosine (designated as the cleavage junction) and Q is dabcyl-dT. LT serves as template to enzymatically ligate DL to FS.

FIG. 5b is a schematic illustration of multi-step DNAzyme selection cycles. Details are described in the experimental section in Example 1E.

FIG. 6a shows sequences of DHp3 and its mutants used for activity comparison. Full-length DHp3, 4 truncated DHp3 variants and 1 mutated DHp3 were compared. Curved dashes denote the truncated nucleotides. The italic small letters in DHp3T4M represent the base mutations.

FIG. 6b shows gel-based activity analysis.

Figure 7A:
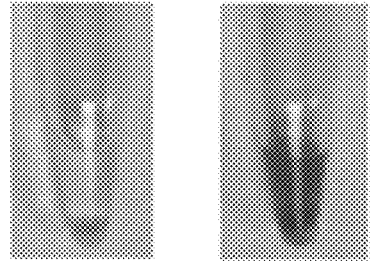

FIG. 7a shows colorimetric test with agarose beads conjugated with urease-containing DHp3T4. Reporting solution before (left) and after (right) the addition of the CEM-HP mediated cleavage reaction solution.

Figure 7B:
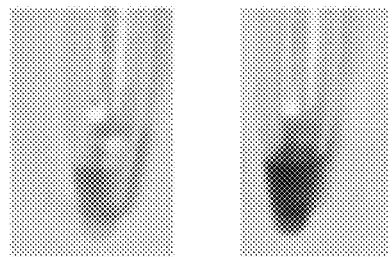

FIG. 7b shows colorimetric test with agarose beads conjugated with urease-containing DHp3T4. Reporting solution before (left) and after (right) the addition of a HP-containing fecal sample.

Figure 8A:
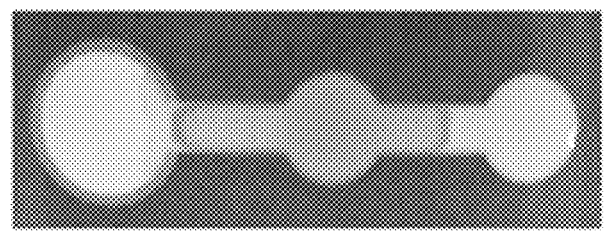

FIG. 8a shows liquid flow of a colored sensing solution in the middle zone and the reporting solution in the detection zone (on the right).

Figure 8B:
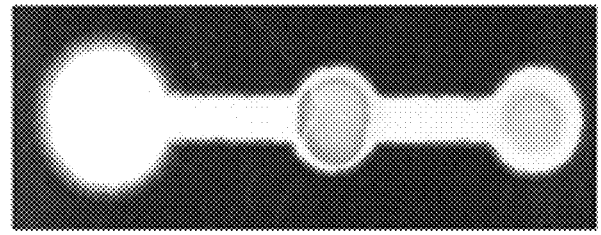

FIG. 8b shows the sensing mixture in the middle zone and the reporting solution in the detection zone (on the right) dissolved from the relevant pullulan films. This is compared with the flow action in FIG. 8a.

Figure 9A:
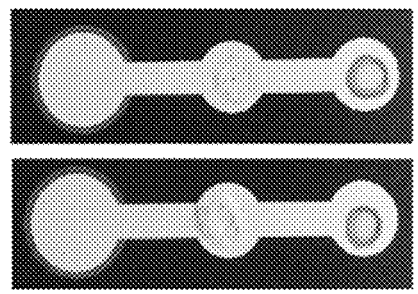

FIG. 9a shows the paper biosensors containing a pullulan film with entrapped DHp3T4-urease-agarose beads in the middle (sensor) zone and a reporting pullulan film in the right (detection) zone prior to addition of sample.

Figure 9B:
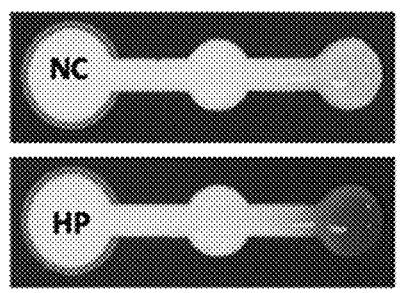

FIG. 9b shows the same biosensor devices in FIG. 9a after addition of either buffer (negative control, NC) or CEM from *H. pylori* (HP) to the sensor zone, incubation for 20 min, followed by addition of 1 mM acetic acid as running buffer to the left zone to cause elution of cleaved urease to the detection zone (on the right) for color development.

Figure 10:
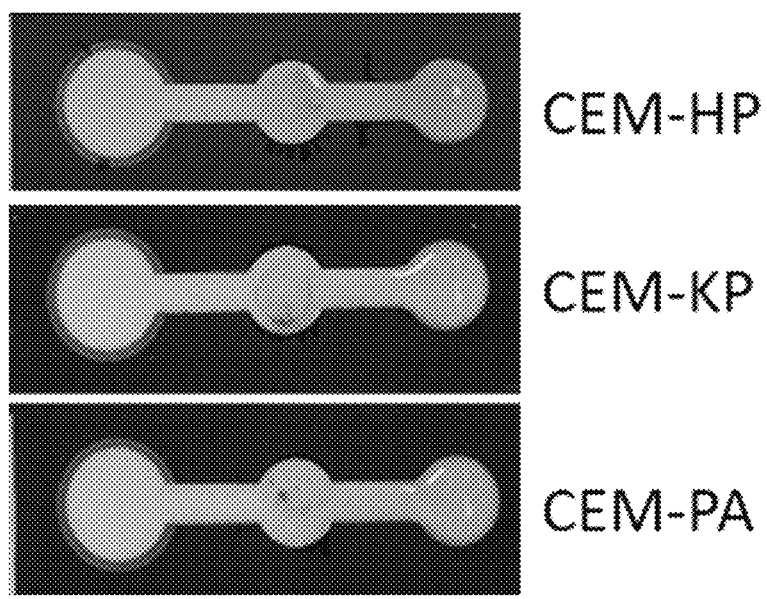

FIG. 10 shows the results of test of color production by CEM alone (endogenous urease) without DNAzyme. CEM: crude extracellular mixture, HP: *H. pylori*, KP: *Klebsiella pneumoniae*, PA: *Pseudomonas aeruginosa*.

Figure 11A:
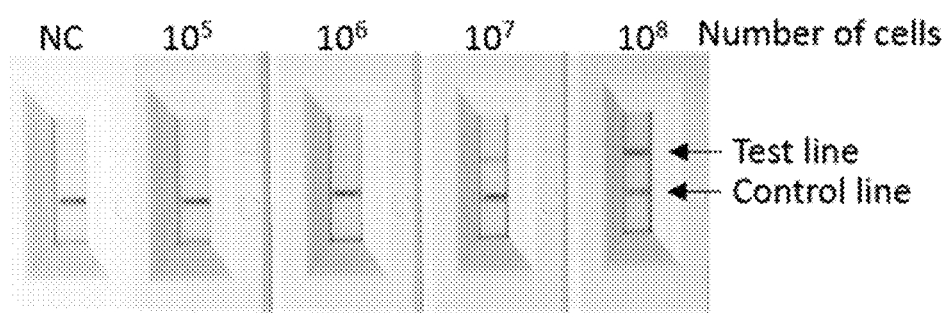

FIG. 11a shows detection limit of HP spiked into human fecal samples using commercially available lateral flow device (ProFlow™). A clear visible signal was only obtained with $10^7$ cfu/mL or higher HP concentrations.

Figure 11B:
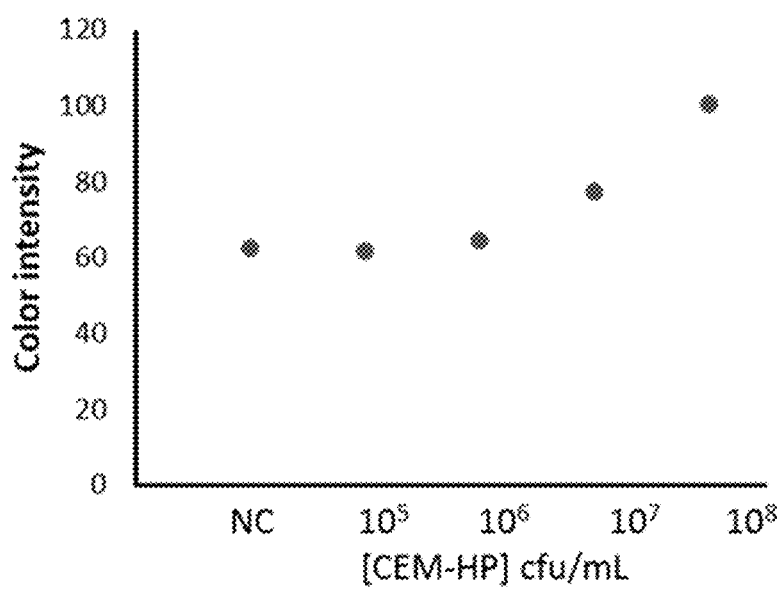

FIG. 11b shows detection limit of HP spiked into human fecal samples in FIG. 11a plotted out in a graph.

Figure 12:
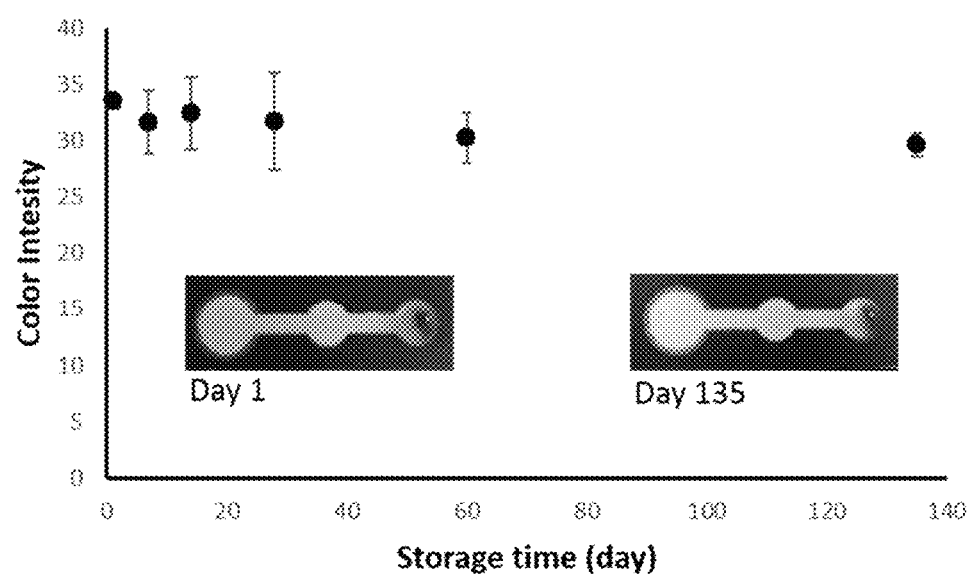

FIG. 12 shows the results of stability testing of the paper-based biosensor device. Sensors were prepared and stored at room temperature (23±1° C.). Their performance was tested at different time points as indicated in the figure. The color intensities for the CEM-HP mediated cleavage reaction were corrected from the negative control where the cleavage reaction was performed using the reaction buffer only. The error bars are standard deviations from experiments done in triplicate.

Figure 13:
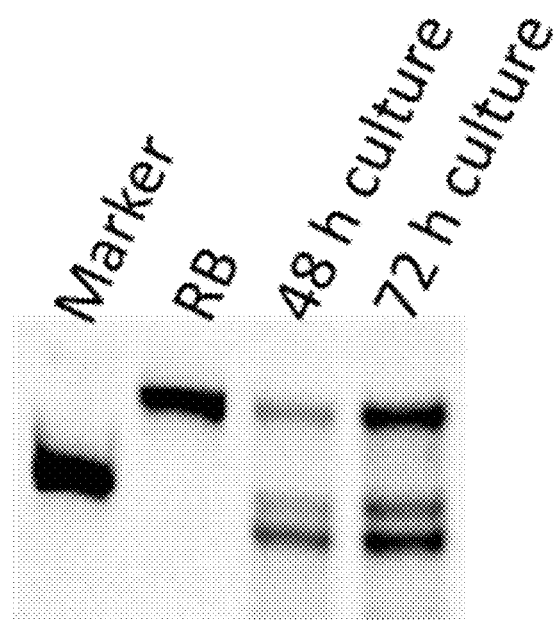

FIG. 13 show the results of cleavage test with CEM-HP after culturing in TSB alone without supplemented sheep's blood for different time periods.

Figure 14:
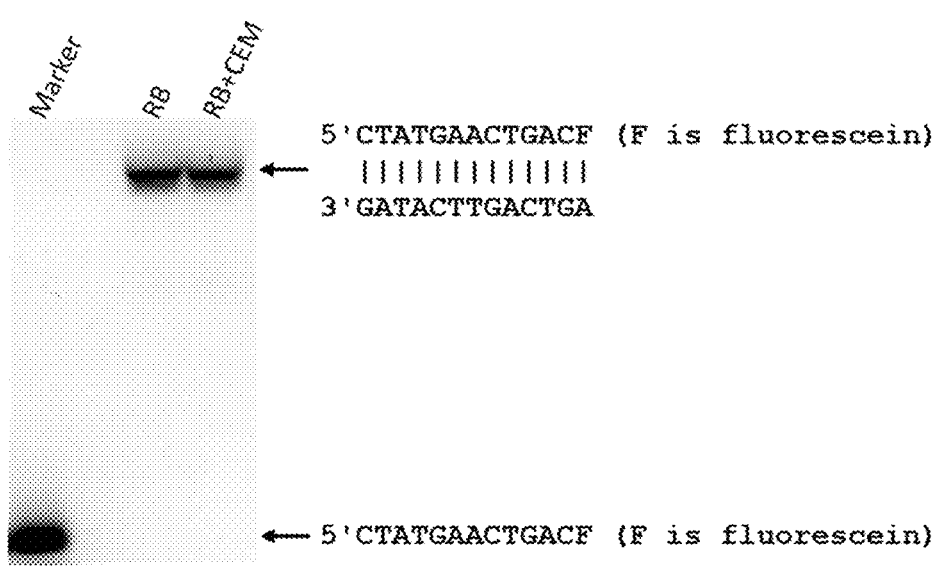

FIG. 14 shows the results of dehybridization test of a short duplex (13 nucleotides) in the absence and presence of CEM-HP by native gel electrophoresis (8% native PAGE).

Figure 15:
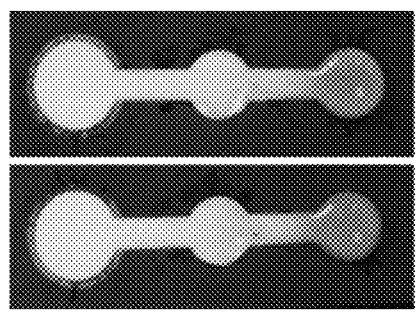

FIG. 15 shows the results of a performance test of the lateral flow biosensor device with fresh and frozen stool samples spiked with CEM-HP at $10^8$ cfu/mL. The sample was kept frozen at −80° C. for 3 days.

DETAILED DESCRIPTION

I. Definitions

Unless otherwise indicated, the definitions and embodiments described in this and other sections are intended to be applicable to all embodiments and aspects of the present disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

The recitation of numerical ranges by endpoints herein includes all numbers and fractions subsumed within that range (e.g. 1 to 5 includes for example 1, 1.5, 2, 2.75, 3, 3.90, 4, and 5). It is also to be understood that all numbers and fractions thereof are presumed to be modified by the term "about".

As used in this disclosure, the singular forms "a", "an" and "the" include plural references unless the content clearly dictates otherwise.

In embodiments comprising an "additional" or "second" component, such as an additional or second component, the second component as used herein is chemically different from the other components or first component. A "third" component is different from the other, first, and second components, and further enumerated or "additional" components are similarly different.

The term "subject" as used herein includes all members of the animal kingdom including mammals such as a mouse, a rat, a dog, and a human.

The term "analyte", "target" or "target molecule" as used herein may refer to any agent, including, but not limited to, a small inorganic molecule, small organic molecule, metal ion, biomolecule, toxin, biopolymer (such as a nucleic acid, carbohydrate, lipid, peptide, protein), cell, tissue, microorganism, virus and pathogen, for which one would like to sense or detect. In an embodiment, the analyte is either isolated from a natural source or is synthetic. The analyte may be a single compound or a class of compounds, such as a class of compounds that share structural or functional features. The term analyte also includes combinations (e.g. mixtures) of compounds or agents such as, but not limited to, combinatorial libraries and samples from an organism or a natural environment. In an embodiment, the analyte comprises a protein.

The term "microorganism" as used herein may refer to a microscopic organism that comprises either a single cell or a cluster of single cells including, but not limited to, bacteria, fungi, archaea, protists, algae, plankton and planarian. In an embodiment, the microorganism is a bacterium. In an embodiment, the microorganism is a pathogenic bacterium (for example, a bacterium that causes bacterial infection), such as *Helicobacter pylori*, *Escherichia coli* O157:H7, *Clostridium difficile*, *Salmonella serovar typhimurium*, *Listeria monocytogenes*, *Klebsiella pneumoniae*, *Fusobacterium nucleatum*, *Pseudomonas aeruginosa*, *Bacteroides fragilis*, *Enterococcus faecium* and *Streptococcus salivarius*.

The term "microorganism target" as used herein may be a molecule, compound or substance that is present in or on a microorganism or is generated, excreted, secreted or metabolized by a microorganism such as a microorganism described herein. In an embodiment, the analyte comprises a microorganism target. In an embodiment, the microorganism target is present in the extracellular matrix of a microorganism. In an embodiment, the microorganism target is present in the intracellular matrix of a microorganism. In another embodiment, the microorganism target comprises a protein, a nucleic acid, a small molecule, extracellular matrix, intracellular matrix, a cell of the microorganism, or any combination thereof. In an embodiment, the microorganism target is a crude or purified extracellular matrix or a crude or purified intracellular matrix. In another embodiment, the microorganism target is specific to a particular species or strain of microorganism. In an embodiment, the microorganism target is a molecule, compound or substance that is present in or on a microorganism or is generated, excreted, secreted or metabolized by a microorganism. In an embodiment, the microorganism target is a molecule, compound or substance that is present in or on any one of *Helicobacter pylori*, *Escherichia coli* O157:H7, *Clostridium difficile*, *Salmonella serovar typhimurium*, *Listeria monocytogenes*, *Klebsiella pneumoniae*, *Fusobacterium nucleatum*, *Pseudomonas aeruginosa*, *Bacteroides fragilis*, *Enterococcus faecium* or *Streptococcus salivarius* or is generated, excreted, secreted or metabolized by any one of *Helicobacter pylori*, *Escherichia coli* O157:H7, *Clostridium difficile*, *Salmonella serovar typhimurium*, *Listeria monocytogenes*, *Klebsiella pneumoniae*, *Fusobacterium nucleatum*, *Pseudomonas aeruginosa*, *Bacteroides fragilis*, *Enterococcus faecium* or *Streptococcus salivarius*. In an embodiment, the microorganism target is a molecule, compound or substance that is present in or on *Helicobacter pylori* or is generated, excreted, secreted or metabolized by *Helicobacter pylori*. In an embodiment, the microorganism target is a molecule, compound or substance that is present in or on *Escherichia coli* O157:H7 or is generated, excreted, secreted or metabolized by *Escherichia coli* O157:H7. In an embodiment, the microorganism target is a molecule, compound or substance that is present in or on *Clostridium difficile* or is generated, excreted, secreted or metabolized by *Clostridium difficile*. In an embodiment, the microorganism target is a molecule, compound or substance that is present in or on *Salmonella serovar typhimurium* or is generated, excreted, secreted or metabolized by *Salmonella serovar typhimurium*. In an embodiment, the microorganism target is a molecule, compound or substance that is present in or on *Listeria monocytogenes* or is generated, excreted, secreted or metabolized by *Listeria monocytogenes*. In an embodiment, the microorganism target is a molecule, compound or substance that is present in or on *Klebsiella pneumoniae* or is generated, excreted, secreted or metabolized by *Klebsiella pneumoniae*. In an embodiment, the microorganism target is a molecule, compound or substance that is present in or on *Fusobacterium nucleatum* or is generated, excreted, secreted or metabolized by *Fusobacterium nucleatum*. In an embodiment, the microorganism target is a molecule, compound or substance that is present in or on *Pseudomonas aeruginosa* or is generated, excreted, secreted or metabolized by *Pseudomonas aeruginosa*. In an embodiment, the microorganism target is a molecule, compound or substance that is present in or on *Bacteroides fragilis* or is generated, excreted, secreted or metabolized by *Bacteroides fragilis*. In an embodiment, the microorganism target is a molecule, compound or substance that is present in or on *Enterococcus faecium* or is generated, excreted, secreted or metabolized by *Enterococcus faecium*. In an embodiment, the microorganism target is a molecule, compound or substance that is present in or on *Streptococcus salivarius* or is generated, excreted, secreted or metabolized by *Streptococcus salivarius*. In an embodiment, the microorganism target is a protein present in or on *Helicobacter pylori* or is generated, excreted, secreted or metabolized by *Helicobacter pylori*. In an embodiment, the microorganism target is a protein present in or on *Escherichia coli* O157:H7 or is generated, excreted, secreted or metabolized by *Escherichia coli* O157:H7. In an embodiment, the microorganism target is a protein present in or on *Clostridium difficile* or is generated, excreted, secreted or metabolized by *Clostridium difficile*. In an embodiment, the microorganism target is a protein present in or on *Salmonella serovar typhimurium* or is generated, excreted, secreted or metabolized by *Salmonella serovar typhimurium*. In an embodiment, the microorganism target is a protein present in or on *Listeria monocytogenes* or is generated, excreted, secreted or metabolized by *Listeria monocytogenes*. In an embodiment, the microorganism target is a protein present in or on *Klebsiella pneumoniae* or is generated, excreted, secreted or metabolized by *Klebsiella pneumoniae*. In an embodiment, the microorganism target is a protein present in or on *Fusobacterium nucleatum* or is generated, excreted, secreted or metabolized by *Fusobacterium nucleatum*. In an embodiment, the microorganism target is a protein present in or on *Pseudomonas aeruginosa* or is generated, excreted, secreted or metabolized by *Pseudomonas aeruginosa*. In an embodiment, the microorganism target is a protein present in or on *Bacteroides fragilis* or is generated, excreted, secreted or metabolized by *Bacteroides fragilis*. In an embodiment, the microorganism target is a protein present in or on *Enterococcus faecium* or is generated, excreted, secreted or metabolized by *Enterococcus faecium*. In an embodiment, the microorganism target is a protein present in or on *Streptococcus salivarius* or is generated, excreted, secreted or metabolized by *Streptococcus salivarius*.

The term "viral target" as used herein may be a molecule, compound or substance that is present in or on a virus or is generated by a virus. In an embodiment, the analyte comprises a viral target.

As used herein, "test sample" refers to a sample in which the presence or amount of an analyte, target, target molecule, or a microorganism target is unknown and to be determined in an assay. The test sample may be a "biological sample" comprising cellular and non-cellular material, including, but not limited to, tissue samples, urine, blood, serum, other bodily fluids, and excrement, such as a stool (i.e. faeces) sample from a subject, or an "environmental sample" obtained from water, soil or air.

As used herein, the term "sensor nucleic acid molecule" refers to a nucleic acid molecule that is DNA, RNA, or a mix of DNA and RNA comprising a first region comprising a nucleic acid-cleaving catalytic nucleic acid probe specific to an analyte, and a second region comprising a nucleic acid sequence having a linkage substrate and a releasable tag nucleic acid molecule. The releasable tag nucleic acid molecule is 5' to the linkage substrate. In an embodiment, the second region is contained on a separate nucleic acid molecule from the first region. This arrangement is referred to as "in trans". In an embodiment, the first region and the second region are in an in trans arrangement. In an "in cis" arrangement, both the first and second regions are present in the same molecule. In an embodiment, the second region is contained on the same nucleic acid molecule from the first region. In an embodiment, the first region and the second region are in an in cis arrangement. The sensor nucleic acid molecule of the present disclosure may be synthesized using oligonucleotide synthesis methods known in the art. The entire sensor nucleic acids may be synthesized as one molecule or the first and second regions may be synthesized separately and combined together, for example by ligation. In an embodiment, the nucleic acid-cleaving catalytic nucleic acid probe comprises a sequence that hybridizes under medium or high stringency conditions to the second region. Medium or high stringency hybridization are well known to persons skilled in the art. Examples of hybridization conditions may be found in molecular biology reference texts such as Molecular Cloning: A Laboratory Manual by Sambrook and Russell (3rd Edition, Cold Spring Harbour Press, 2001). For example, high stringency conditions comprise the following: hybridization at 5× sodium chloride/sodium citrate (SCC)/5× Denhardt's solution/1.0% SDS at Tm −5° C. for 15 minutes based on the equation (Tm=81.5° C.−16.6 (Log 10 [Na+])+0.41(% G+C)−600/1) (or similar equation)), followed by a wash of 0.2×SSC/0.1% SDS at 60° C. It is understood, however, that equivalent stringencies may be achieved using alternative buffers, salts and temperatures.

As used herein, the term "nucleic acid-cleaving catalytic nucleic acid probe" refers to DNA (i.e. DNAzyme) or RNA (i.e. ribozyme) that can cleave a substrate that is DNA or RNA upon contacting an analyte. The substrate can be a linkage substrate that links two regions of a single nucleic acid molecule.

The term "linkage substrate" as used herein refers to a substrate that can be cleaved by a nucleic acid-cleaving catalytic nucleic acid probe. The linkage substrate can be a ribonucleotide linkage substrate, and the ribonucleotide linkage substrate can have a riboadenosine (also known as adenine ribonucleotide) serving as the cleavage junction. The linkage substrate links the nucleic acid-cleaving catalytic nucleic acid probe to the releasable tag nucleic acid molecule. The releasable tag nucleic acid molecule can directly conjugate a reporter, or indirectly conjugate a reporter through an adapter nucleic acid molecule. The releasable tag nucleic acid molecule can be between 20 and 50 nucleotides in length of any sequence provided that the corresponding adapter nucleic acid molecule disclosed herein has a complementary sequence or a portion thereof, or sufficient complementarity that provides a strong enough interaction to prevent dehybridization. The adapter nucleic acid molecule is a nucleic acid molecule that has a complementary sequence to the releasable tag nucleic molecule or a portion thereof, or sufficient complementarity that provides a strong enough interaction to prevent dehybridization, As used herein, the term "DNAzyme" or deoxyribozyme refers to DNA oligonucleotides that are capable of performing or catalyzing a specific chemical reaction, similar to the action of biological enzymes, which are proteins and ribozymes, upon detecting an analyte. DNAzymes differ from DNA aptamers which are oligonucleotides that selectively bind a target ligand, but do not catalyze a subsequent chemical reaction. The present inventors have identified DNAzymes that can be a part of a sensor nucleic acid molecule capable of cleaving a linkage substrate upon binding to an analyte.

As used herein, the term "ribozyme" refers to RNA molecules that have the ability to catalyze specific biochemical reactions similar to the action of protein enzymes.

II. Lateral Flow Biosensor Device, DNAzymes, Probes and Biosensors of the Disclosure The lateral flow biosensor device described herein is intended for rapid detection of the presence of an analyte in a test sample without the need for costly or sophisticated equipment. This device is useful in laboratory testing, point-of-care applications, or medical diagnostics for home testing. The lateral flow biosensor device described herein comprises a sensor zone having an immobilized and stabilized biosensor, and a detection zone having stabilized reporting solution.

In a broad aspect, herein provided is a lateral flow biosensor device for detecting the presence of an analyte in a test sample, comprising:
  i) a buffer zone for applying a running buffer, the buffer zone being connected through a flow channel to ii) a sensor zone for applying a test sample comprising an immobilized biosensor entrapped by a stabilizing matrix, the sensor zone being connected through a flow channel to iii) a detection zone for indicating the presence or a range of levels of the analyte,
  wherein the immobilized biosensor in the sensor zone is immobilized to a solid support, and the immobilized biosensor comprises:
    a) a sensor nucleic acid molecule comprising a first region comprising a nucleic acid-cleaving catalytic nucleic acid probe specific to the analyte, and a second region comprising a nucleic acid sequence having a linkage substrate and a releasable tag nucleic acid molecule, and
    b) a reporter conjugated to the releasable tag nucleic acid molecule of the sensor nucleic acid molecule or an adapter nucleic acid molecule conjugated with a reporter,
  wherein the adapter nucleic acid molecule comprises a nucleic acid sequence complementary to the releasable tag nucleic acid molecule or a portion thereof, or sufficient complementarity that provides a strong enough interaction to prevent dehybridization,
  wherein the adapter nucleic acid molecule hybridizes to the releasable tag nucleic acid molecule to form a releasable fragment comprising the reporter,
  wherein, in the presence of analyte, the nucleic acid-cleaving catalytic nucleic acid probe is activated and cleaves the linkage substrate at a cleavage site, thereby releasing the releasable tag nucleic acid molecule conjugated with the reporter or the releasable fragment comprising the reporter, and
  wherein, upon cleavage, the releasable tag nucleic acid molecule conjugated with the reporter or the releasable fragment comprising the reporter migrates to the detection zone due to lateral flow of the running buffer and produces a signal.

In an embodiment, the first region comprising the nucleic acid-cleaving catalytic nucleic acid probe that detects the analyte is 5 to 500, 10 to 200, 20 to 120, or 22 to 100 base pairs in length. In an embodiment, the first region comprises a sequence with at least 80%, 90%, 95% or 99% sequence identity to any one of SEQ ID NO: 1-14 or 28-36. In an embodiment, the first region comprises a sequence with optionally at least 5, 10, 15, 20, 30, 40, 50, 60, 70, 80, 90 or 100 base pairs that are contiguous with sequences contained in any one of SEQ ID NO: 1-14 or 28-36. In other embodiments, the first region comprises or consists of any one of SEQ ID NO: 1-14 or 28-36. In an embodiment, the first region has catalytic activity such that it modifies a substrate upon detecting the analyte. In an embodiment, the second region comprising the substrate is 25 to 100 or 40 to 80 base pairs in length.

In an embodiment, the releasable tag nucleic acid molecule is about 20 to about 50 nucleotides. In an embodiment, the adapter nucleic acid molecule comprises a nucleic acid sequence complementary to the releasable tag nucleic acid molecule or a portion thereof, or sufficient complementarity that provides a strong enough interaction to prevent dehybridization.

A number of solid supports are useful for immobilizing the biosensor, for example, agarose beads, silica beads, sepharsose beads, synthetic polymer beads or any other bead material so long as the diameter is sufficiently large to prevent movement during buffer flow. The immobilization of the biosensor to a solid support can be achieved through different means, including using molecular interaction that has a low dissociation constant such as a covalent interaction, for example, by way of biotin-streptavidin interaction. Immobilizing the biosensor can also be achieved by coating the paper surface (can be selectively printed on the sensor zone) with avidin or streptavidin and bind the biosensor through a biotin linkage, or even covalently immobilize the biosensor to the paper through any standard coupling reactions. The skilled person would recognize any method to immobilize the biosensor to the paper surface, the detection zone of the lateral flow biosensor device. Accordingly, in an embodiment, the biosensor is immobilized to the solid support, such as agarose beads, silica beads, sepharsose beads, synthetic polymer beads or any other bead material which diameter is sufficiently large to prevent movement during buffer flow, or directly to the paper surface of the lateral flow biosensor device, through covalent or strong non-covalent interaction. In an embodiment, the solid support comprises agarose beads, silica beads, sepharsose beads, synthetic polymer beads or any other bead material which diameter is sufficiently large to prevent movement during buffer flow. In an embodiment, the solid support comprises agarose beads. In an embodiment, the biosensor is immobilized to the agarose beads by biotin-streptavidin interaction. In an embodiment, the solid support comprises agarose beads, and the biosensor is immobilized to the agarose beads by biotin-streptavidin or biotin-avidin interaction. In an embodiment, the biosensor is immobilized to the agarose beads by biotin-streptavidin. In an embodiment, the support solid is a paper surface of the lateral flow biosensor device. In an embodiment, the biosensor is immobilized directly to the paper surface of the lateral flow biosensor device described herein.

The analyte in the test sample can be a small inorganic molecule, small organic molecule, metal ion, biomolecule, toxin, or biopolymer. The biopolymer can be a nucleic acid, carbohydrate, lipid, peptide, or protein. Accordingly, in an embodiment, the analyte is a small inorganic molecule, small organic molecule, metal ion, biomolecule, toxin, or biopolymer. In an embodiment, the biopolymer is a nucleic acid, carbohydrate, lipid, peptide, or protein. In an embodiment, the analyte is a protein.

In an embodiment, the detection zone comprises a stabilizing matrix and a reporting solution. The stabilizing matrix of the sensor zone and the detection zone provides viscosity such that there is minimal diffusion out of their respective zones in the lateral flow biosensor device. The stabilizing matrix also provides stability to the immobilized biosensor in the sensor zone and the reporting solution in the detection zone, so to provide long shelf life for the lateral flow biosensor device. As such, a suitable material for stabilizing matrix is a material that has a viscosity of between 10-50 centipoise, and provides stability to the immobilized biosensor in the sensor zone and the reporting solution in the detection zone for at least four months. When the reporter disclosed herein is an enzyme, a suitable material for stabilizing matrix is a material that is also oxygen impermeable so to prevent oxidation of enzymes and components in the reporting solution. A number of materials can serve as stabilizing matrix, for example, pullulan, polyethylene glycol (PEG), or other suitable polymers readily recognize by the person skilled in the art. The lateral flow biosensor device described herein can use pullulan to stabilize the biosensor and reporting solution in the sensor zone and detection zone, respectively, through the formation of a film. Pullulan is a polysaccharide polymer consisting of maltotriose units. Three glucose units in maltotriose are connected by an α-1,4 glycosidic bond, and consecutive maltotriose units in pullulan are connected to each other by an α-1,6 glycosidic bond. Accordingly, in an embodiment, the stabilizing matrix is oxygen impermeable. One exemplary stabilizing matrix is a pullulan film which has a low oxygen permeability of 0.5 cc/m²·24 h·atm at 60% relative humidity and 25° C. and a suitable viscosity, such as 10-50 centipoise. Accordingly, in an embodiment, the stabilizing matrix has a viscosity of between 10-50 centipoise. In another embodiment, the stabilizing matrix comprises pullulan. In one embodiment, the pullulan is at 2.5 wt %. In another embodiment, the pullulan is pullulan PF-20. In an embodiment, the stabilizing matrix provides stability to the immobilized biosensor in the sensor zone and the reporting solution in the detection zone for at least four, six, eight, ten, or twelves months, and up to thirty-six months. In an embodiment, the stabilizing matrix provides stability to the immobilized biosensor in the sensor zone and the reporting solution in the detection zone for at least four months and up to thirty-six months. In an embodiment, the stabilizing matrix provides stability to the immobilized biosensor in the sensor zone and the reporting solution in the detection zone for at least six months and up to thirty-six months. In an embodiment, the stabilizing matrix provides stability to the immobilized biosensor in the sensor zone and the reporting solution in the detection zone for at least eight months and up to thirty-six months. In an embodiment, the stabilizing matrix provides stability to the immobilized biosensor in the sensor zone and the reporting solution in the detection zone for at least ten months and up to thirty-six months. In an embodiment, the stabilizing matrix provides stability to the immobilized biosensor in the sensor zone and the reporting solution in the detection zone for at least twelve months and up to thirty-six months. In an embodiment, the stabilizing matrix is oxygen impermeable, has a viscosity of between 10-50 centipoise, and provides stability to the immobilized biosensor in the sensor zone and the reporting solution in the detection zone for at least four, six, eight, ten, or twelves months, and up to thirty-six months.

A number of materials are useful for making the lateral flow biosensor device described herein. For example, the present inventors have created a lateral flow biosensor comprising separated zones and flow channels. Such zones and flow channels can be created by wax on a nitrocellulose paper backed with a plastic sheet, i.e. wax acts as a uniform hydrophobic barrier for which the running buffer does not penetrate and the nitrocellulose paper acts to allow lateral flow of the running buffer. For example, the design shown in FIG. 4a was wax-printed on nitrocellulose paper backed with a plastic sheet and then heated at 110° C. for 2 min to diffuse the wax through the nitrocellulose membrane to create a uniform hydrophobic barrier (black region). Other methods for creating a hydrophobic barrier on a support layer are known to the person skilled in the art. The skilled person also recognizes that many alternatives to nitrocellulose paper are possible, for example, any material that allows flow could work, such as cellulose, or any other surface that supports capillary flow. Accordingly, in an embodiment, the lateral flow biosensor device comprises nitrocellulose paper, cellulose, or any surface that supports capillary flow. In an embodiment, the lateral flow biosensor device comprises nitrocellulose paper. In an embodiment, the lateral flow biosensor device comprises a polymer support layer. In an embodiment, the polymer support layer comprises a plastic sheet. In an embodiment, the lateral flow biosensor device comprises a hydrophobic material. In an embodiment, the hydrophobic material comprises wax. In an embodiment, the lateral flow biosensor device was printed by a hydrophobic material. In an embodiment, the lateral flow biosensor device was printed by wax.

A useful linkage substrate for the sensor nucleic acid molecule described herein includes a ribonucleotide linkage substrate. Accordingly, in an embodiment, the linkage substrate comprises a ribonucleotide linkage substrate. In an embodiment, the ribonucleotide linkage substrate comprises a cleavage site for a nucleic acid-cleaving catalytic nucleic acid probe. In an embodiment, the cleavage site is a riboadenosine. In an embodiment, the ribonucleotide linkage substrate comprises a riboadenosine. In an embodiment, the ribonucleotide linkage substrate comprises at least 80%, 90%, 95% or 99% sequence identity or consisting of a sequence of SEQ ID NO: 26 or a functional fragment or modified derivative thereof.

The nucleic acid-cleaving catalytic nucleic acid probe can be a DNAzyme or a ribozyme. Accordingly, in an embodiment, the nucleic acid-cleaving catalytic nucleic acid probe is a DNAzyme. In an embodiment, the DNAzyme comprises a sequence of any one of SEQ ID NO: 1-14 or 28-36, or a functional fragment or modified derivative thereof. In an embodiment, the DNAzyme comprises or consists of a sequence of SEQ ID NO: 1, or a functional fragment or modified derivative thereof. In an embodiment, the DNAzyme comprises or consists of a sequence of SEQ ID NO: 2, or a functional fragment or modified derivative thereof. In an embodiment, the DNAzyme comprises or consists of a sequence of SEQ ID NO: 3, or a functional fragment or modified derivative thereof. In an embodiment, the DNAzyme comprises or consists of a sequence of SEQ ID NO: 4, or a functional fragment or modified derivative thereof. In an embodiment, the DNAzyme comprises or consists of a sequence of SEQ ID NO: 5, or a functional fragment or modified derivative thereof. In an embodiment, the DNAzyme comprises or consists of a sequence of SEQ ID NO: 6, or a functional fragment or modified derivative thereof. In an embodiment, the DNAzyme comprises or consists of a sequence of SEQ ID NO: 7, or a functional fragment or modified derivative thereof. In an embodiment, the DNAzyme comprises or consists of a sequence of SEQ ID NO: 8, or a functional fragment or modified derivative thereof. In an embodiment, the DNAzyme comprises or consists of a sequence of SEQ ID NO: 9, or a functional fragment or modified derivative thereof. In an embodiment, the DNAzyme comprises or consists of a sequence of SEQ ID NO: 10, or a functional fragment or modified derivative thereof. In an embodiment, the DNAzyme comprises or consists of a sequence of SEQ ID NO: 11 or a modified derivative thereof. In an embodiment, the DNAzyme comprises or consists of a sequence of SEQ ID NO: 12 or a modified derivative thereof. In an embodiment, the DNAzyme comprises or consists of a sequence of SEQ ID NO: 13 or a modified derivative thereof. In an embodiment, the DNAzyme comprises or consists of a sequence of SEQ ID NO: 14 or a modified derivative thereof. In an embodiment, the DNAzyme comprises or consists of a sequence of SEQ ID NO: 28 or a modified derivative thereof. In an embodiment, the DNAzyme comprises or consists of a sequence of SEQ ID NO: 29 or a modified derivative thereof. In an embodiment, the DNAzyme comprises or consists of a sequence of SEQ ID NO: 30 or a modified derivative thereof. In an embodiment, the DNAzyme comprises or consists of a sequence of SEQ ID NO: 31 or a modified derivative thereof. In an embodiment, the DNAzyme comprises or consists of a sequence of SEQ ID NO: 32 or a modified derivative thereof. In an embodiment, the DNAzyme comprises or consists of a sequence of SEQ ID NO: 33 or a modified derivative thereof. In an embodiment, the DNAzyme comprises or consists of a sequence of SEQ ID NO: 34 or a modified derivative thereof. In an embodiment, the DNAzyme comprises or consists of a sequence of SEQ ID NO: 35 or a modified derivative thereof. In an embodiment, the DNAzyme comprises or consists of a sequence of SEQ ID NO: 36 or a modified derivative thereof. In an embodiment, the nucleic acid-cleaving catalytic nucleic acid probe comprises a ribozyme.

In an embodiment, the reporter is a reporter enzyme or a gold nanoparticle.

In one embodiment, the reporter is a reporter enzyme. In one embodiment, the detection zone comprises a reporting solution entrapped by a stabilizing matrix. In an embodiment, the reporter is a reporter enzyme. In an embodiment, the reporter enzyme reacts with the reporting solution in the detection zone to produce a signal. The reporter enzyme can be any enzyme that is capable of producing a detectable signal with the appropriate substrates. The components of the reporter solution depends on the enzymatic specificity of the reporter enzyme. In an embodiment, the reporter enzyme is urease and the reporting solution includes urea and a pH sensitive dye. In an embodiment, the pH sensitive dye is phenol red, bromothymol blue, 6,8-dinitro-2,4-(1H)quinazolinedione, brilliant yellow, neutral red, m-nitrophenol, cresol red, naphtholphthalein, phenolphthalein, m-cresol purple, or o-cresolphthalein complexone. In another embodiment, the reporter enzyme is alkaline phosphatase and the reporting solution comprises 5-Bromo-4-chloro-3-indolyl phosphate along with nitro blue tetrazolium (BCIP/NBT), para-Nitrophenylphosphate (pNPP), or Fast Red. In yet another embodiment, the reporter enzyme is cholinesterase and the reporting solution comprises indoxylacetate 5,5'-dithiobis(2-nitrobenzoic acid) (DTNB). In an embodiment, the cholinesterase is at least one of acetylcholinesterase and butyrylcholinesterase. In a further embodiment, the reporter enzyme is horseradish peroxidase and the reporting solution comprises hydrogen peroxide and least one of 3,3',5,5'-Tetramethylbenzidine, 3,3',5,5'-Tetramethylbenzidine, and 2,2'-azino-bis(3 -ethylbenzothiazoline-6-sulfonic acid. In an embodiment, the signal is color or color change.

In an embodiment, the reporter is a gold nanoparticle. In an embodiment, the releasable tag nucleotide acid molecule is conjugated with gold nanoparticles and upon cleavage, the releasable tag nucleotide acid molecule flows to the detection zone where a signal is detected. In an embodiment, the cleavage site of the linking substrate is flanked at the 5' and 3' each by a nucleotide conjugated with a gold nanoparticle. In an embodiment, the adapter nucleic acid molecule is conjugated with a gold nanoparticle, wherein the adapter nucleic acid molecule is hybridized to the releasable tag nucleic acid molecule to form a releasable fragment comprising the gold nanoparticle, and upon cleavage, the releasable fragment flows to the detection zone where a signal is detected. In an embodiment, the signal is color or color change.

A number of running buffer solutions are useful as a running buffer for the lateral flow biosensor device described herein. For example, acetic acid is useful as a running buffer, such as acetic acid at 1 mM or any weak acid. The skilled person would readily recognize that buffer compatible with DNAzyme function would be suitable as running buffer, and the skilled person would readily recognize such a buffer. In an embodiment, the running buffer comprises acetic acid or a weak acid. In an embodiment, the running buffer comprises acetic acid. In an embodiment, the acetic acid is at about 1 mM.

The analyte that can be detected by the lateral flow biosensor device described herein can be a molecule, compound or substance that is present in or on a microorganism, or is generated, excreted, secreted or metabolized by a microorganism. In an embodiment, the analyte comprises a molecule, compound or substance that is present in or on a microorganism, or is generated, excreted, secreted or metabolized by a microorganism. In an embodiment, the microorganism is *Helicobacter pylori, Escherichia coli* O157:H7, *Clostridium difficile, Salmonella serovar typhimurium, Listeria monocytogenes, Klebsiella pneumoniae, Fusobacterium nucleatum, Pseudomonas aeruginosa, Bacteroides fragilis, Enterococcus faecium* or *Streptococcus salivarius*. In an embodiment, the microorganism is *Helicobacter pylori*. In an embodiment, the microorganism is *Escherichia coli* O157:H7. In an embodiment, the microorganism is *Clostridium difficile*. In an embodiment, the microorganism is *Salmonella serovar typhimurium*. In an embodiment, the microorganism is Listeria monocytogenes. In an embodiment, the microorganism is *Klebsiella pneumoniae*. In an embodiment, the microorganism is *Fusobacterium nucleatum*. In an embodiment, the microorganism is *Pseudomonas aeruginosa*. In an embodiment, the microorganism is *Bacteroides fragilis*. In an embodiment, the microorganism is *Enterococcus faecium*. In an embodiment, the microorganism is *Streptococcus salivarius*. In a specific embodiment, the microorganism is *Helicobacter pylori,* and the nucleic acid-cleaving catalytic nucleic acid probe comprises a sequence of any one of SEQ ID NO: 1-14 or 28-36, or a functional fragment or modified derivative thereof.

Also provided is a kit for detecting a microorganism, wherein the kit comprises the lateral flow biosensor device described herein, one or more components required thereof, and instructions for use of the kit for detecting the microorganism. In embodiment, the one or more components required comprises a running buffer. In embodiment, the running buffer comprises acetic acid or a weak acid. In embodiment, the running buffer comprises 1 mM acetic acid.

In an aspect, the disclosure provides a DNAzyme that detects with and is activated by a protein biomarker from *Helicobacter pylori*. The inventors identified in an in vitro screening assay a number of DNAzymes that are activated by a protein biomarker from *Helicobacter pylori,* namely DHp01 (SEQ ID NO: 1), DHp02 (SEQ ID NO: 2), DHp03 (SEQ ID NO: 3), DHp04 (SEQ ID NO: 4), DHp05 (SEQ ID NO: 5), DHp06 (SEQ ID NO: 6), DHp07 (SEQ ID NO: 7), DHp08 (SEQ ID NO: 8), DHp09 (SEQ ID NO: 9), and DHp10 (SEQ ID NO: 10). The DNAzymes identified in this disclosure cleaves a DNA/RNA sequence having a ribonucleotide cleavage site, such as a riboadenosine cleavage site. The DNAzymes identified herein cleave a RNA sequence comprising or consisting of SEQ ID NO: 26, or a functional fragment or modified derivative thereof. In an embodiment, the DNAzyme that detects and is activated by *Helicobacter pylori* comprises or consists of any one of sequence of SEQ ID Nos: 1-10, or a functional fragment or modified derivative thereof. In an embodiment, the DNAzyme that detects and is activated by *Helicobacter pylori* comprises or consists of a sequence of SEQ ID NO: 1, or a functional fragment or modified derivative thereof. In an embodiment, the DNAzyme that detects and is activated by s *Helicobacter pylori* comprises or consists of a sequence of SEQ ID NO: 2, or a functional fragment or modified derivative thereof. In an embodiment, the DNAzyme that detects and is activated by *Helicobacter pylori* comprises or consists of a sequence of SEQ ID NO: 3, or a functional fragment or modified derivative thereof. In an embodiment, the DNAzyme that detects and is activated by *Helicobacter pylori* comprises or consists of a sequence of SEQ ID NO: 4, or a functional fragment or modified derivative thereof. In an embodiment, the DNAzyme that detects and is activated by *Helicobacter pylori* comprises or consists of a sequence of SEQ ID NO: 5, or a functional fragment or modified derivative thereof. In an embodiment, the DNAzyme that detects and is activated by *Helicobacter pylori* comprises or consists of a sequence of SEQ ID NO: 6, or a functional fragment or modified derivative thereof. In an embodiment, the DNAzyme that detects and is activated by *Helicobacter pylori* comprises or consists of a sequence of SEQ ID NO: 7, or a functional fragment or modified derivative thereof. In an embodiment, the DNAzyme that detects and is activated by *Helicobacter pylori* comprises or consists of a sequence of SEQ ID NO: 8, or a functional fragment or modified derivative thereof. In an embodiment, the DNAzyme that detects and is activated by *Helicobacter pylori* comprises or consists of a sequence of SEQ ID NO: 9, or a functional fragment or modified derivative thereof. In an embodiment, the DNAzyme that detects and is activated by *Helicobacter pylori* comprises or consists of a sequence of SEQ ID NO: 10, or a functional fragment or modified derivative thereof. In an embodiment, the DNAzyme detects and is activated by a protein of *Helicobacter pylori*.

The present inventors have further made truncated sequences of DHp03 that are capable of detecting and being activated by *Helicobacter pylori*. The active truncated sequences of DHp03 identified include DHp3T1 (SEQ ID NO: 11), DHp3T2 (SEQ ID NO: 12), DHp3T3 (SEQ ID NO: 13), and DHp3T4 (SEQ ID NO: 14). Accordingly, in an embodiment, the DNAzyme that detects and is activated by *Helicobacter pylori* comprises or consists of any one of sequence of SEQ ID Nos: 11-14, a functional fragment or modified derivative thereof. In an embodiment, the DNAzyme that detects and is activated by *Helicobacter pylori* comprises or consists of a sequence of SEQ ID NO: 11, a functional fragment or modified derivative thereof. In an embodiment, the DNAzyme that detects and is activated by *Helicobacter pylori* comprises or consists of a sequence of SEQ ID NO: 12, a functional fragment or modified derivative thereof. In an embodiment, the DNAzyme that detects and is activated by *Helicobacter pylori* comprises or consists of a sequence of SEQ ID NO: 13, a functional fragment or modified derivative thereof. In an embodiment, the DNAzyme that detects and is activated by *Helicobacter pylori* comprises or consists of a sequence of SEQ ID NO: 14, a functional fragment or modified derivative thereof. In an embodiment, the DNAzyme detects and is activated by a protein of *Helicobacter pylori*.

Methods for identifying active truncated sequences of the other DNAzymes DHp01, DHp02, DHp04, DHp05, DHp06, DHp07, DHp08, DHp09, and DHp10 disclosed herein may similarly be optimized, for example, by the method undertook by the present inventors in Example 1G.

The random region of DHp01, DHp02, DHp04, DHp05, DHp06, DHp07, DHp08, DHp09, and DHp10 are shown in SEQ ID NOS: 28-36. Accordingly, in an embodiment, the DNAzyme that detects and is activated by *Helicobacter pylori* comprises or consists of any one of sequence of SEQ ID Nos: 28-36 or a modified derivative thereof. In an embodiment, the DNAzyme that detects and is activated by *Helicobacter pylori* comprises or consists of a sequence of SEQ ID NO: 28 or a modified derivative thereof. In an embodiment, the DNAzyme that detects and is activated by *Helicobacter pylori* comprises or consists of a sequence of SEQ ID NO: 29 or a modified derivative thereof. In an embodiment, the DNAzyme that detects and is activated by *Helicobacter pylori* comprises or consists of a sequence of SEQ ID NO: 30 or a modified derivative thereof. In an embodiment, the DNAzyme that detects and is activated by *Helicobacter pylori* comprises or consists of a sequence of SEQ ID NO: 31 or a modified derivative thereof. In an embodiment, the DNAzyme that detects and is activated by *Helicobacter pylori* comprises or consists of a sequence of SEQ ID NO: 32 or a modified derivative thereof. In an embodiment, the DNAzyme that detects and is activated by *Helicobacter pylori* comprises or consists of a sequence of SEQ ID NO: 33 or a modified derivative thereof. In an embodiment, the DNAzyme that detects and is activated by *Helicobacter pylori* comprises or consists of a sequence of SEQ ID NO: 34 or a modified derivative thereof. In an embodiment, the DNAzyme that detects and is activated by *Helicobacter pylori* comprises or consists of a sequence of SEQ ID NO: 35 or a modified derivative thereof. In an embodiment, the DNAzyme that detects and is activated by *Helicobacter pylori* comprises or consists of a sequence of SEQ ID NO: 36 or a modified derivative thereof. The skilled person can readily recognize that the random region that detects and is activated by *Helicobacter pylori* can have additional surrounding sequence at the 5' and 3' ends (see Table 4). Accordingly, in an embodiment, the DNAzyme that detects and is activated by *Helicobacter pylori* comprises any one of sequence of SEQ ID NOs: 13 or 28-36, further comprises a sequence of any one of SEQ ID NOs: 37-52 at the 5' end, and a sequence of any one of SEQ ID NOs: 53-66 at the 3' end. In an embodiment, the DNAzyme detects and is activated by a protein of *Helicobacter pylori*.

The DNAzyme described herein can be a nucleic acid-cleaving catalytic nucleic acid probe that is a part of a sensor nucleic acid molecule. Accordingly, also provided herein is a sensor nucleic acid molecule comprises a first region comprising a nucleic acid-cleaving catalytic nucleic acid probe specific to the analyte, and a second region comprising a nucleic acid sequence having a linkage substrate and a releasable tag nucleic acid molecule. Accordingly, also provided is a sensor nucleic acid molecule comprising a first region comprising a nucleic acid-cleaving catalytic nucleic acid probe having a sequence of any one of SEQ ID NO: 1-14 or 28-36, or a functional fragment or modified derivative thereof, and a second region comprising a nucleic acid sequence having a linkage substrate and a releasable tag nucleic acid molecule. In an embodiment, the first region comprising a nucleic acid-cleaving catalytic nucleic acid probe having a sequence of SEQ ID NO: 1, or a functional fragment or modified derivative thereof. In an embodiment, the first region comprising a nucleic acid-cleaving catalytic nucleic acid probe having a sequence of SEQ ID NO: 2, or a functional fragment or modified derivative thereof. In an embodiment, the first region comprising a nucleic acid-cleaving catalytic nucleic acid probe having a sequence of SEQ ID NO: 3, or a functional fragment or modified derivative thereof. In an embodiment, the first region comprising a nucleic acid-cleaving catalytic nucleic acid probe having a sequence of SEQ ID NO: 4, or a functional fragment or modified derivative thereof. In an embodiment, the first region comprising a nucleic acid-cleaving catalytic nucleic acid probe having a sequence of SEQ ID NO: 5, or a functional fragment or modified derivative thereof. In an embodiment, the first region comprising a nucleic acid-cleaving catalytic nucleic acid probe having a sequence of SEQ ID NO: 6, or a functional fragment or modified derivative thereof. In an embodiment, the first region comprising a nucleic acid-cleaving catalytic nucleic acid probe having a sequence of SEQ ID NO: 7, or a functional fragment or modified derivative thereof. In an embodiment, the first region comprising a nucleic acid-cleaving catalytic nucleic acid probe having a sequence of SEQ ID NO: 8, or a functional fragment or modified derivative thereof. In an embodiment, the first region comprising a nucleic acid-cleaving catalytic nucleic acid probe having a sequence of SEQ ID NO: 9, or a functional fragment or modified derivative thereof. In an embodiment, the first region comprising a nucleic acid-cleaving catalytic nucleic acid probe having a sequence of SEQ ID NO: 10, or a functional fragment or modified derivative thereof. In an embodiment, the first region comprising a nucleic acid-cleaving catalytic nucleic acid probe having a sequence of SEQ ID NO: 11, or a functional fragment or modified derivative thereof. In an embodiment, the first region comprising a nucleic acid-cleaving catalytic nucleic acid probe having a sequence of SEQ ID NO: 12, or a functional fragment or modified derivative thereof. In an embodiment, the first region comprising a nucleic acid-cleaving catalytic nucleic acid probe having a sequence of SEQ ID NO: 13, or a functional fragment or modified derivative thereof. In an embodiment, the first region comprising a nucleic acid-cleaving catalytic nucleic acid probe having a sequence of SEQ ID NO: 14, or a functional fragment or modified derivative thereof. In an embodiment, the first region comprising a nucleic acid-cleaving catalytic nucleic acid probe having a sequence of SEQ ID NO: 28, or a functional fragment or modified derivative thereof. In an embodiment, the first region comprising a nucleic acid-cleaving catalytic nucleic acid probe having a sequence of SEQ ID NO: 29, or a functional fragment or modified derivative thereof. In an embodiment, the first region comprising a nucleic acid-cleaving catalytic nucleic acid probe having a sequence of SEQ ID NO: 30, or a functional fragment or modified derivative thereof. In an embodiment, the first region comprising a nucleic acid-cleaving catalytic nucleic acid probe having a sequence of SEQ ID NO: 31, or a functional fragment or modified derivative thereof. In an embodiment, the first region comprising a nucleic acid-cleaving catalytic nucleic acid probe having a sequence of SEQ ID NO: 32, or a functional fragment or modified derivative thereof. In an embodiment, the first region comprising a nucleic acid-cleaving catalytic nucleic acid probe having a sequence of SEQ ID NO: 33, or a functional fragment or modified derivative thereof. In an embodiment, the first region comprising a nucleic acid-cleaving catalytic nucleic acid probe having a sequence of SEQ ID NO: 34, or a functional fragment or modified derivative thereof. In an embodiment, the first region comprising a nucleic acid-cleaving catalytic nucleic acid probe having a sequence of SEQ ID NO: 35, or a functional fragment or modified derivative thereof. In an embodiment, the first region comprising a nucleic acid-cleaving catalytic nucleic acid probe having a sequence of SEQ ID NO: 36, or a functional fragment or modified derivative thereof. In an embodiment, the linkage substrate is a ribonucleotide linkage substrate. In an embodiment, the linkage substrate comprises a ribonucleotide linkage substrate. In an embodiment, the ribonucleotide linkage substrate comprises a cleavage site for a nucleic acid-cleaving catalytic nucleic acid probe described in this disclosure. In an embodiment, the cleavage site is a riboadenosine. In an embodiment, the ribonucleotide linkage substrate comprises a riboadenosine. In an embodiment, the ribonucleotide linkage substrate comprises at least 80%, 90%, 95% or 99% sequence identity or consisting of a sequence of SEQ ID NO: 26, or a functional fragment or modified derivative thereof.

The sensor nucleic molecule described herein can be a part of a biosensor for detecting *Helicobacter pylori* in a test sample. Accordingly, also provided in this disclosure is a biosensor for detecting *Helicobacter pylori* in a test sample, comprising:
  i) a sensor nucleic acid molecule described herein attached to a solid support; and
  ii) a reporter conjugated to the releasable tag nucleic acid molecule of the sensor nucleic acid molecule or an adapter nucleic acid molecule conjugated with a reporter,
  wherein the adapter nucleic acid molecule comprises a nucleic acid sequence complementary to the releasable tag nucleic acid molecule or a portion thereof, or sufficient complementarity that provides a strong enough interaction to prevent dehybridization,
  wherein the adapter nucleic acid molecule hybridizes to the releasable tag nucleic acid molecule to form a releasable fragment comprising the reporter,
  wherein, in the presence of analyte, the nucleic acid-cleaving catalytic nucleic acid probe is activated and cleaves the linkage substrate at a cleavage site, thereby releasing the releasable tag nucleic acid molecule conjugated with the reporter, or the releasable fragment comprising the reporter available for detection or detection reaction.

In an embodiment, the adapter nucleic acid molecule comprises a nucleic acid sequence complementary to the releasable tag nucleic acid molecule or a portion thereof, or sufficient complementarity that provides a strong enough interaction to prevent dehybridization. In an embodiment, the adapter nucleic acid molecule hybridizes to the releasable tag nucleic acid molecule. In an embodiment, the test sample is a stool sample. In an embodiment, the reporter is a reporter enzyme or a gold nanoparticle. In an embodiment, the reporter is a reporter enzyme. In an embodiment, the reporter is a gold nanoparticle. In an embodiment, the solid support are agarose beads. In an embodiment, the reporter enzyme comprises urease. In an embodiment, detection comprises measuring color changes using urea and a pH sensitive dye. In an embodiment the pH sensitive dye comprises phenol red. In an embodiment, color intensity is indicative of amount of analyte. In an embodiment, the solid support are agarose beads, the reporter enzyme comprises urease, the detection comprises measuring color changes using urea and phenol red, and color intensity is indicative of amount of analyte. The amount of analyte can be measured, for example, by the method in Example 1R which captures the image using a camera from a cell phone and processed by imaging software and plotted using spreadsheet software. Other routine methods for measuring the amount of analyte can be readily identified by a skilled person.

Also provided is a kit for detecting a microorganism, wherein the kit comprises the biosensor described herein, one or more components required thereof, and instructions for use of the kit for detecting the microorganism.

III. Methods

Also provided is a method of detecting a microorganism in a test sample, comprising:

applying the test sample to a sensor zone of a lateral flow biosensor device described herein, wherein the test sample comprises an analyte from a microorganism, wherein the analyte contacts the immobilized biosensor in the sensor zone and activates the nucleic acid-cleaving nucleic acid probe which cleaves the linkage substrate at a cleavage site and releases a fragment comprising the reporter enzyme, applying a running buffer to the buffer zone of the lateral flow biosensor device, whereby the running buffer laterally flows into the sensor zone and the released fragment comprising the reporter then moves laterally to a detection zone, allowing the reporter to produce a signal, and detecting the signal in the detection zone.

In an embodiment, the signal is a color change signal. In an embodiment, color is indicative of amount of analyte. In an embodiment, the reporter is a reporter enzyme or a gold nanoparticle. The reporter enzyme can be any enzyme that is capable of producing a detectable signal with the appropriate substrates. The components of the reporter solution depends on the enzymatic specificity of the reporter enzyme. In an embodiment, the reporter enzyme is urease, alkaline phosphatase, cholinesterase, or horseradish peroxidase, and components of the reporter solution described herein that allow production of such a detectable signal. In an embodiment, the microorganism is *Helicobacter pylori*, *Escherichia coli* O157:H7, *Clostridium difficile*, *Salmonella serovar typhimurium*, *Listeria monocytogenes*, *Klebsiella pneumoniae*, *Fusobacterium nucleatum*, *Pseudomonas aeruginosa*, *Bacteroides fragilis*, *Enterococcus faecium* or *Streptococcus salivarius*. In an embodiment, the microorganism is *Helicobacter pylori*. In an embodiment, the microorganism is *Escherichia coli* O157:H7. In an embodiment, the microorganism is *Clostridium difficile*. In an embodiment, the microorganism is *Salmonella serovar typhimurium*. In an embodiment, the microorganism is *Listeria monocytogenes*. In an embodiment, the microorganism is *Klebsiella pneumoniae*. In an embodiment, the microorganism is *Fusobacterium nucleatum*. In an embodiment, the microorganism is *Pseudomonas aeruginosa*. In an embodiment, the microorganism is *Bacteroides fragilis*. In an embodiment, the microorganism is *Enterococcus faecium*. In an embodiment, the microorganism is *Streptococcus salivarius*. In a specific embodiment, the microorganism is *Helicobacter pylori*, and the nucleic acid-cleaving catalytic nucleic acid probe comprises a sequence of any one of SEQ ID NO: 1-14 or 28-36, or a functional fragment or modified derivative thereof.

EXAMPLES

The following non-limiting examples are illustrative of the present disclosure:

Example 1. A DNAzyme-Based Colorimetric Paper Sensor for *Helicobacter pylori*

EXPERIMENT SECTION Example 1A. DNA Oligonucleotides

The random DNA library (DL) and the fluorogenic substrate (FS) were purchased from the Keck Oligo Synthesis Facilities, Yale University (New Haven, Conn.). The forward PCR primer (FP; SEQ ID NO: 23), two reverse PCR primers [RP1 (SEQ ID NO: 24) and RP2 (SEQ ID NO: 25)], and ligation template (LT) were obtained from Integrated DNA technologies (IDT; Coralville, Iowa). All the sequences are shown in FIG. 5a. Each oligonucleotide of the DL contains 80 nucleotides (nt) including a random-sequence domain of 50 nt (denoted as N50) in the center and two constant regions of 16 nt and 14 nt at the 5' and 3' ends, respectively. Each random position, N, represents a 25% probability of A, C, G or T nucleotides. The 28-nt FS (SEQ ID NO: 26) contains a riboadenosine nucleotide (rA) that serves as the cleavage site. rA is flanked by a fluorescein-dT (F) and a dabcyl-dT (Q). RP1 and RP2 are two reverse primers used in PCR. RP2 contains a poly-A tail (A20) at the 5' end separated by a hexaethylene glycol spacer (L). The spacer prevents the poly-A tail from being amplified and thus makes the non-coding strand 20 nucleotides longer than the coding strand (DNAzyme), which allows for facile purification of the desired coding sequence by denaturing polyacrylamide gel electrophoresis (dPAGE) (more details are provided below in the in vitro selection procedure in Example 1E). RDL, FP, RP1, RP2 and LT were purified by 10% dPAGE before use.

Example 1B. Enzymes and Chemicals

T4 DNA ligase and T4 polynucleotide kinase including their respective buffers were purchased from Thermo Scientific. Unless otherwise noted, all other chemicals were purchased either from Bioshop Canada or from Sigma-Aldrich and used without further purification. Water used in this work was double-deionized (ddH$_2$O) and autoclaved.

Example 1C. Bacterial cells

*Helicobacter pylori* (J99) (HP), *Escherichia coli* O157:H7 (EC), *Clostridium difficile* (CD), *Salmonella serovar typhimurium* (ST), *Bacillus subtilis* (BS), *Listeria monocytogenes* (LM), *Klebsiella pneumoniae* (KP), *Fusobacterium nucleatum* (FN), *Pseudomonas aeruginosa* (PA), *Bacteroides fragilis* (BF), *Enterococcus faecium* (EF) and *Streptococcus salivarius* (SS) were purchased from ATCC and are routinely maintained in inventors' lab.

Example 1D. Preparation of Crude Extracellular Mixtures (CEMs).

CEMs from the above bacteria were prepared as follows: Each of the bacteria were grown in individual culture tubes in 5 mL tryptic soy broth (TSB) including 2% sheep blood with continuous shaking at 37° C. and 250 rpm until the OD of the culture reached ~2, corresponding to approximately 10$^8$ cfu/mL. The cells were precipitated by centrifugation at 11,000 g for 5 min at room temperature. The supernatants were collected and passed through a 0.2 micron molecular size cut-off filter disc, aliquoted into microcentrifuge tubes (100 µL each) and stored at −20° C. until use.

Example 1E. In vitro Selection

For schematic illustration of in vitro selection of DNAzyme, see FIG. 5b. Library preparation and selection (step I). For the first round of selection, 1000 pmol of DL was ligated to FS as follows: DL was phosphorylated in a 100 µL reaction volume using T4 Polynucleotide Kinase for 45 min at 37° C. in the supplied 1× T4 polynucleotide kinase buffer A in the presence of 1 mM ATP. The reaction was stopped by heating at 90° C. for 5 min. Equivalent amounts of FS and LT (1000 pmol each) were added to this solution and the mixture was heated at 90° C. for 40 s and cooled to room temperature for 20 min. Then, 30 µL of the supplied 10× T4 DNA ligase buffer, 30 µL of PEG4000 and 5 µL (25 U) of T4 DNA ligase were added. The volume was adjusted to 300 µL with ddH$_2$O, mixed by pipetting and incubated at room temperature for 1 h.

Purification of ligated FS-DL (step II). The DNA molecules in the reaction mixture from step I were isolated by ethanol precipitation and the ligated FS-DL molecules were purified by 10% dPAGE. This DNA pool was dissolved in 200 µL of 1× selection buffer (1× SB; 50 mM HEPES, pH 7.5, 150 mM NaCl, 15 mM MgCl$_2$, and 0.01% Tween 20).

Negative selection (step III). 50 µL of a mixture of CEM of control bacteria (ST, EC, LM, CD and BS) was mixed with 50 µL of 2× SB and added to the FS-DL pool of step II (the total volume becomes 300 µL). After mixing by pipetting, the reaction mixture was incubated at room temperature for 2 h. The reaction was quenched by the addition of 30 µL of 3.0 M NaOAc followed by 890 µL of cold ethanol.

Purification of uncleaved FS-DL (step IV). After ethanol precipitation, the reaction mixture was subjected to 10% dPAGE and visualized by imaging the intrinsic fluorescence of the bound FAM dye. The uncleaved FS-DL molecules were isolated.

Positive selection (step V). The purified uncleaved DNA pool from step IV was dissolved in 100 µL of 1× SB. Immediately, 100 µL of CEM-HP in 1× SB (50 µL CEM-HP mixed with 50 µL 2× SB) was added to the DNA pool. After mixing by pipetting, the reaction mixture was incubated at room temperature for 60 min. The reaction was stopped by adding 20 µL of NaOAc followed by 590 µL of cold ethanol.

Isolation of cleaved products (step VI). After ethanol precipitation, the reaction mixture was subjected to 10% dPAGE. In the first few rounds, little cleavage activity was expected, and for this reason, excision of the cleavage fragment was assisted through the use of a DNA marker corresponding to the cleavage product. This marker was prepared by treating a small portion of the FS-DL with 0.25 M NaOH at 90° C. for 10 min. The cleavage product was excised, recovered by ethanol precipitation, and dissolved in 50 µL ddH$_2$O.

PCR1 (step VII). The PCR was typically conducted in a volume of 50 µL with 10 µL of the cleavage fragment from step VI, 0.5 µM each of FP and RP1, 200 µM dNTPs (dATP, dCTP, dGTP and dTTP), 1× PCR buffer (75 mM Tris-HCl, pH 9.0, 2 mM MgCl$_2$, 50 mM KCl, 20 mM (NH$_4$)$_2$SO$_4$) and 2.5 units of *Thermus thermophilus* DNA polymerase (Biotools, Madrid, Spain). The amplification was conducted using the following thermocycling parameters: one cycle of 94° C. for 1 min; 13-15 cycles of 94° C. for 30 s, 50° C. for 45 s and 72° C. for 45 s (the numbers of amplification cycles between different selection rounds were adjusted, typically between 13 and 15 cycles, to achieve full amplification as assessed by 2% agarose gel electrophoresis); one cycle of 72° C. for 1 min.

PCR2 (step VIII). Because of the requirement for a large amount of DNA molecules, a second PCR was conducted in 20 tubes with 50 uL volume in each using the PCR1 product as a template. In this case, 1 µL of the PCR1 product was diluted to 20 µL, 1 µL of which was used in PCR2 using FP and RP2 primers following the same amplification parameters as PCR1 (note that the numbers of amplification cycles between different selection rounds were adjusted, typically between 13 and 15 cycles, to achieve full amplification, as assessed by 2% agarose gel electrophoresis).

Purification of DNAzyme-coding strand (step IX). The PCR2 product was concentrated by ethanol precipitation and subjected to 10% dPAGE. The DNA band of the coding strand (shorter sequence, bottom band) was excised and the DNA was eluted and stored at −20° C. as a dry pellet until use.

Ligation of PCR product to FS (step X) and repetition of steps II-X. The coding DNA strand prepared above (approximately 200 pmol, stored as a dried pellet) was ligated to FS as follows: the DNA was phosphorylated in a 100 µL reaction volume with 10 U of polynucleotide kinase in the presence of 1 mM ATP in 1× kinase buffer A for 40 min at 37° C. Note that the reaction volume of phosphorylation for round 2 and after was constantly maintained at 100 µL. The phosphorylation reaction was quenched by heating at 90° C. for 5 min and cooled down to room temperature for 20 min. Equal amounts of FS and LT (200 pmol each) were added to the reaction mixture, mixed by vortexing, heated at 90° C. for 1 min and cooled to room temperature for 20 min. Then, 20 µL of 10× ligase buffer, 20 µL of PEG4000 and 4 µL of T4 DNA ligase were added and the volume of the reaction was adjusted to 200 µL with ddH$_2$O (ligations for the subsequent selection rounds were carried out in 200 µL volume). After mixing by pipetting, the ligation reaction was conducted at room temperature for 1 h. After ethanol precipitation the ligated DNA product was purified by 10% dPAGE and employed in the second round of selection following the same procedure as described for the first round. Note that the negative selection step was applied every two rounds of selection.

Example 1F. Screening for the Most Active DNAzyme

The round-12 DNA pool was sequenced and the top 10 candidates were identified based on the sequence frequency, which was scored based on the number of times a particular sequence was identified in the sequencing pool (their names and sequences are shown in Table 1, i.e. SEQ ID Nos: 1-10). These sequences were chemically synthesized, ligated to FS and tested for cleavage performance (FIG. 1c). 1000 nmol of each DNAzyme was ligated to FS as described above in the selection procedure. After ligation and purification, the DNAzyme sequences were dissolved in ddH$_2$O, quantified using a Tecan nano-quant system (M200, Bio-Rad) and stored at −20° C. until use. The concentration of each candidate was adjusted to 2 µM by diluting with ddH$_2$O. Typically, for each DNAzyme two cleavage reactions were conducted in a 10 µL volume: one with reaction buffer only (control) and another with CEM-HP (test). 1 µL of each DNAzyme was mixed with 5 µL of 2× SB. The cleavage reaction was started by adding 4 µL of ddH$_2$O to the control and 4 µL of CEM-HP to the test. After 45 min at room temperature, the cleavage reaction was quenched by adding 10 µL of 2× denaturing gel loading buffer (2× GLB; 90 mM Tris-base, 90 mM Boric acid, 2 mM EDTA, 14 M Urea, 0.5 M sucrose, 0.1% SDS, 0.03% of xylene cyanol and 0.03% of bromophenol blue). The reaction mixtures were subjected to 10% dPAGE and the gel was scanned for fluorescence using a ChemiDoc fluorescent imager (Bio-Rad).

Example 1G. Sequence Truncation and Specificity Test of DHp3

The most active DNAzyme DHp3 was chosen for sequence truncation and mutation (FIG. 6a). The activity of these mutants was tested in the same way as described above (FIG. 6b). The most active truncated sequence was named DHp3T4 (FIG. 1d shows DHp3T4 with FQ-substrate (SEQ ID NO: 27); DHp3T4 is shown in SEQ ID NO: 14 Biotin-FQ-substrate DHp3T4 (B-DHp3T4-FS2) is shown in SEQ ID NO: 20) and was used for all subsequent experiments. Selectivity was tested with CEM prepared from different bacteria. First, each of the bacteria were cultured in TSB media (except HP, which was cultured in TSB including 2% sheep blood as recommended by ATCC) for different time points to reach an OD of ~2 (corresponds to ~$10^8$ cells/mL). One milliliter of each culture was centrifuged at 11,000 g for 5 min to precipitate the cells. The supernatant was used as the CEM of this bacterium. Next the cleavage reactions were carried out as follows: 5 µL of 2× SB was mixed with 1 µL of DHp3T4 (2 µM stock) and 4 µL of a relevant CEM. A control experiment was also conducted with 1× SB alone. The reaction mixtures were incubated at room temperature for 30 min and quenched by adding 10 µL of 2× GLB. The reaction mixtures were analyzed by 10% dPAGE and the gel was scanned for fluorescence using a ChemiDoc fluorescent imager (Bio-Rad).

Example 1H. Assessment of Putative DNAzyme Targets

SDS experiment: 1µL of 10% SDS was added to 10 µL of CEM-HP and mixed by pipetting. The final concentration of SDS in the CEM was 1%. This CEM was incubated at room temperature for 30 min. 4 µL of thus treated CEM was mixed with 5 µL of 2× SB and 1 µL (2 µM stock) of the DHp3T4. The reaction mixture was incubated at room temperature for 45 min, quenched by adding 10 µL of 2× GLB, and then subjected to 10% dPAGE analysis.

EDTA experiment: 1 µL (2 µM stock) of the DHp3T4 was mixed with 5 µL of 2× SB, 1 µL of 300 mM EDTA and 4 µL of CEM-HP (final EDTA concentration=30 mM). The reaction mixture was incubated at room temperature for 45 min, quenched by adding 10 µL of 2× GLB, and then subjected to 10% dPAGE analysis.

Ribolock experiment: 5 µL of 2× SB was mixed with 4 µL of CEM-HP and 1 µL (40 U/µL) of ribolock (Thermofisher, Canada). The reaction mixture was incubated at RT for 30 min. Next, 1 µL of DHp3T4 (2 µM) was added and mixed by pipetting. The reaction mixture was incubated at room temperature for 45 min, quenched by adding 10 µL of 2× GLB, and then subjected to 10% dPAGE analysis.

Proteinase K (PK) experiment: 4 µL of CEM-HP was mixed with 5 µL of 2× SB and 1 µL of proteinase K (30 mg/mL, Thermo Scientific), and the mixture was incubated at 37° C. for 1 h. 1 µL of DHp3T4 (2 µM) was then added and mixed by pipetting. The mixture was incubated at RT for 45 min. The reaction mixture was incubated at room temperature for 45 min, quenched by adding 10 µL of 2× GLB, and then subjected to 10% dPAGE analysis.

RNase I experiment: 1 µL of DHp3T4 (2 µM) was mixed with 5 µL 2× SB, 3 µL of ddH$_2$O and 1 µL of RNase I (10 U/µL, Thermo Scientific). The reaction mixture was incubated at room temperature for 45 min, quenched by adding 10 µL of 2× GLB, and then subjected to 10% dPAGE analysis.

RNase I+SDS experiment: 1 µL of RNase I was mixed with 1 µL of 1% SDS and 2 µL volume in ddH$_2$O for 30 min, followed by the addition of 1 µL of DHp3T4 (2 µM) and 5 µL 2× SB. The reaction mixture was incubated at room temperature for 45 min, quenched by adding 10 µL of 2× GLB, and then subjected to 10% dPAGE analysis RNase I treatment to remove RNA from CEM: 2 µL (20 units) of RNase I was mixed with 50 µL of CEM-HP and incubated at room temperature for 1 h. Next, 3 µL of ribolock (30 units) was added to the CEM and incubated at room temperature for 30 min to inactivate RNase I. The cleavage reaction was carried out as follows: 1 µL (2 pmol) of DHp3T4 was dispensed in a microcentrifuge tube followed by sequential addition of 5 µL of 2× SB and 4 µL of the above RNase I treated CEM. After mixing by pipette, the reaction mixture was incubated at room temperature for 30 min. The reaction was quenched by adding 10 µL of 2× GLB and applied to 10% dPAGE.

DNase I treatment to remove DNA from CEM: 2 µL (10 units) of DNase I was mixed with 50 µL of CEM-HP and incubated at room temperature for 1 h. Next, 0.5 µL of 10% SDS (0.1% final concentration) was added to the CEM and incubated at room temperature for 10 min to inactivate DNase I. The cleavage reaction was carried out as follows: 1 µL (2 pmol) of DHp3T4 was dispensed in a microcentrifuge tube followed by sequential addition of 5 µL of 2× SB and 4 µL of the above DNase I treated CEM. After mixing by pipette, the reaction mixture was incubated at room temperature for 30 min. The reaction was quenched by adding 10 µL of 2× GLB and applied to 10% dPAGE.

See FIG. 1e for the results of assessment of the nature of the target that activates DHp3T4.

Example 1I. Molecular Size Determination

100 µL of CEM-HP was passed through 30K, 50K and 100K molecular sizing columns (Amicon Ultra-0.5 centrifugal columns from EMD Millipore) for 10 min at 10,000 rpm. The filtrate from each column was collected and used in the DNAzyme cleavage reaction as follows: 1 µL (2 µM) of DHp3T4 was mixed with 5 µL of 2× SB. 4 0 µL of a relevant filtrate was added and the reaction mixture was incubated at room temperature for 45 min, quenched by adding 10 µL of 2× GLB, and then subjected to 10% dPAGE analysis. See FIG. 1f for estimation of the molecular weight of the target.

Example 1J. Selectivity Test

10 µL of CEM of each bacterium was mixed with 1 µL of 10% SDS and incubated for 30 min. 4 µL of this CEM was mixed with 5 µL of 2× SB and 1 µL (2 µM stock) of the DHp3T4. The reaction mixture was incubated at room temperature for 45 min, quenched by adding 10 µL of 2× GLB, and then subjected to 10% dPAGE analysis. See FIG. 1g for the results of the specificity test.

Example 1K. Fluorescence Assay

See the top of FIG. 2 for fluorescence assay signaling reaction. Fluorescence production of DHp3T4 in the presence of different HP concentrations was analyzed in a 96 well plate (flat black, clear bottom) using a Tecan plate reader (M200, Bio-Rad). The HP concentration was determined by the conventional cell counting method. Briefly, HP was cultured in 3 mL of TSB including 2% sheep blood for 72 h at 37° C. with shaking (250 rpm). Next, this culture was serially diluted 8 times with TSB, using a 10-fold dilution each time. The last 3 dilutions (100 μL) were spread in tryptic soy agar (TSA) plates (performed in triplicate). The plates were incubated at 37° C. for 18 h and the colonies were counted to derive the cell concentration in the original culture (which was found to be ~$10^9$ cells/mL). Next, 90 μL of each dilution was dispensed in a well of the 96-well plate. The plate reading was done with the following parameters: excitation 488 nm, emission 520 nm, reading from bottom, gain 150, signal acquisition every minute for 90 min duration, and shaking for 1 sec before measurement. The plate was inserted and data collection was carried out for 5 min without DNAzyme. Next 2.5 μL (2 μM) of DHp3T4 (SEQ ID NO: 14) was added to each well and data collection was continued for another 80 min. The data was saved as spread sheet and processed using Microsoft Excel™ software. See the bottom of FIG. 2 for the results of fluorescence response of DHp3T4 to various concentrations of HP.

Example 1L. Establishing a Reaction Buffer Compatible with the Colorimetric Assay The DNAzyme was selected in the presence of 1× SB, which contained 50 mM HEPES, pH 7.5, 150 mM NaCl, 15 mM $MgCl_2$, and 0.01% Tween 20. To reduce the impact of the high concentration of HEPES buffer on the reporting assay, the HEPES concentration was reduced from 50 mM to 1 mM and found that the DNAzyme remained fully active in the presence of the modified reaction buffer named 1× MRB (1 mM HEPES, 150 mM NaCl, 15 mM $MgCl_2$, 0.02% Tween 20, pH 7.5).

Example 1L. Preparing the Sensing Material for Colorimetric Test

Preparation of urease DNA conjugate: The urease-DNA conjugate was prepared following the previously reported protocol (ref 10a in the main text). Briefly, a bifunctional cross-linker with terminal maleimide and NHS groups (known as N-γ-maleimidobutyryl-oxysulfosuccinimide ester: Sulfo-GMBS from Thermo Scientific) was first reacted with the amine modified adapter DNA (AdDNA in Table 2; SEQ ID NO: 16) and purified. Next, this maleimide-DNA was subjected to a thiol-coupling reaction with urease via the maleimide group in a slightly acidic buffer (pH 6.5), passed through a centrifugal 50K molecular sizing column and washed with water. The conjugate was suspended in ddH₂O and stored at 4° C.

Ligation of biotinylated DHp3T4 to FS2: To immobilize the DNAzyme onto agarose beads, a 3'-biotinylated DHp3T4 (BDHp3T4 in Table 2; SEQ ID NO: 18) and a modified substrate (FS2 in Table 2; SEQ ID NO: 17) were ligated together to form B-DHp3T4-FS (SEQ ID NO: 20) as follows: 1000 pmol of BDHp3T4 was phosphorylated using 20 Units of T4 polynucleotide kinase in 100 μL 1× kinase buffer A in the presence of 1 mM ATP at 37° C. for 45 min. The reaction was stopped by heating at 90° C. for 5 min followed by cooling to room temperature for 20 min. Next, an equal amount of LT (SEQ ID NO: 19; sequence is shown in Table 2) was added to the reaction mixture, heated at 90° C. for 1 min and cooled at room temperature for 20 min. Then 30 μL PEG4000, 30 μL 10× T4 DNA ligase buffer and 5 μL (25 U) of T4 DNA ligase were sequentially added to the reaction mixture. After mixing by pipetting, the reaction mixture was incubated at room temperature for 1 h. The reaction was quenched by adding 30 μL of 3.0 M NaOAc followed by 890 μL of cold ethanol. The DNA molecules were isolated by centrifugation and purified by 10% dPAGE. The purified DNA molecules were dissolved in ddH₂O and quantified using a nano-quant as described above. The sample was labeled as BDHp3T4-FS2 and stored at −20° C. until use Immobilization of BDHp3T4-FS2 onto agarose beads and hybridization with urease-AdDNA conjugate: Pierce streptavidin agarose beads used for this experiment were purchased from Thermo Scientific. The average size of the particles 100 microns with a range of 45 to 165 microns. 50 μL of stock streptavidin coated agarose bead suspension was transferred to a fresh microcentrifuge tube and washed twice with 300 μL of 1× MRB. The agarose beads were suspended in 300 μL of 1× MRB; 50 μL of BDHp3T4-FS2 (10 μM stock) was then added to the beads, and the mixture was mildly shaken at room temperature for 1 h. The beads were sedimented by brief centrifugation using a bench top mini centrifuge. The supernatant was discarded and the beads were washed 3 times with 300 μL of 1× MRB. The bead-bound DNAzyme was denoted as SA-DHp3T4-FS2. The SA-DHp3T4-FS2 was suspended in 300 μL of 1× MRB, followed by the addition of 50 μL of AdDNA-Urease conjugate (8 μM). The suspension was gently shaken in a rocker for 2 h. The beads were sedimented by brief centrifugation using a bench top mini centrifuge and the supernatant was discarded by pipette. The beads were washed until the supernatant did not change the color of the reporting solution (0.75 mM acetic acid, 7.5 mM urea, 0.02% phenol red). Usually, this required 5 washes. Finally, the beads were suspended in 500 μL of 1× MRB. This complex was denoted as DHp3T4-Ur-SA and stored at 4° C. until use.

Example 1M. Cleavage and Color Development with HP Spiked Stool Sample

Stool samples used in this study were provided by Pro-Lab Diagnostics, Ontario, Canada. The samples were found to be HP negative using a commercially available HP lateral flow device (Proflow™, from Pro-Lab Diagnostics, Ontario, Canada). HP cells were cultured for 72 h in TSB media including 2% sheep blood. The cells were quantified by the conventional serial dilution method as described above and the concentration was found to be 2.0×$10^9$ per milliliter. The spiked stool samples were prepared by mixing equal volumes of whole bacteria culture and stool sample and were frozen at −80° C. until used. To test the cleavage reaction and color development, 10 μL of the bead suspension was taken in a centrifuge tube and 10 μL of the thawed spiked stool sample was mixed with 10 μL of 2× MRB and added to the bead suspension. The reaction mixture was incubated at room temperature for 20 min with occasional mixing using a pipette to prevent sedimentation of the beads. Next, the beads were sedimented by brief centrifugation using a benchtop mini centrifuge followed by resting on the bench top for 5 min. 5 μL of the reaction mixture was carefully withdrawn by pipette and added to a tube that contained 50 μL of the reporting solution. The color development was observed and captured using a cell phone camera (Samsung Galaxy S3™). See FIG. 7a and FIG. 7b for the results. FIG. 7a shows the results from the addition of the CEM-HP mediated cleavage reaction solution. FIG. 7b shows the results from the addition of a HP-containing fecal sample.

Example 1N. Selectivity and Sensitivity Test using Spiked Stool Sample in Solution To test the selectivity, the cleavage reaction and color development were carried out with a series of bacteria spiked stool samples as indicated in FIG. 3b in the main text. All the bacteria were cultured in TSB (in the case of HP, 2% sheep blood was included in TSB) to have each culture at ~$10^9$ cells/mL. 50 µL of culture was mixed with 50 µL 2× MRB and used in the cleavage and color development reaction. The cleavage and color development reactions were as described in the above section for HP. To test the assay sensitivity, a series of diluted HP culture solutions were prepared as described above. 50 µL of stool sample was mixed with 40 µL of dd$H_2O$ and 10 µL of a relevant HP solution. 10 µL of HP-containing stool sample was mixed with 10 µL of the DHp3T4-Ur-SA suspension obtained above and 10 µL of 2× MRB. The reaction was conducted at room temperature for 20 min with occasional pipetting to prevent the beads from sedimentation. After brief centrifugation using a benchtop mini centrifuge, the beads were rested on the bench top for 5 min to sediment the beads. 10 µL of the clear supernatant was carefully withdrawn from each tube and added to the color development tube that contained 50 µL of the reporting solution as described above. The color was captured using Samsung Galaxy S3™ and processed by ImageJ and plotted using Microsoft Excel™ software (FIG. 3c). Each experiment was conducted in triplicate to obtain standard deviations (error bars).

Example 1O. Design of Paper Biosensor Device

The paper biosensor design was drawn using Microsoft PowerPoint™ with a black background providing 3 spherical zones all interconnected through a flow channel (zones and the connecting channels are white, FIG. 4a). Zone 1 (10 mm diameter) serves as a buffer loading zone, zone 2 (5 mm diameter in the middle) serves as the sensor zone and zone 3 (far right zone, 5 mm diameter) serves as the detection zone, respectively. The connecting channel was 3 mm wide. This design was wax-printed on nitrocellulose paper backed with a plastic sheet and then heated at 110° C. for 2 min to diffuse the wax through the nitrocellulose membrane to create a uniform hydrophobic barrier (black region).

Example 1P. Fabrication of Paper Biosensor Device with Pullulan Films

To create a sensor film, DHp3T4-Ur-SA was homogeneously suspended in 500 µL of 1× MRB. In parallel, 500 µL of 5 wt % pullulan in 1× MRB was also prepared. 100 µL of SA-BDHp3T4-Ur suspension was mixed with 100 µL of the pullulan solution (final concentration of pullulan becomes 2.5 wt %) in a tube. 20 µL of this suspension was dispensed onto a hydrophobic plastic sheet and air dried to form a colorless, transparent film. To form a reporting film, a 2.5 wt % pullulan solution including 1.0 mM acetic acid, 7.5 mM urea and 0.02% of phenol red (yellow form) was prepared in a tube. 20 µL of this solution was dispensed onto a plastic sheet and air dried to form a film with a yellow color. Next, both films were attached onto their respective zones using 1 µL of water, air dried and stored at room temperature until use, as detailed below (also see FIG. 8a, FIG. 8b, FIG. 9a, and FIG. 9b).

Example 1Q. Cleavage Test Through Color Development

A volume of 10 µL of spiked stool sample was mixed with 10 µL of 2× MRB, added onto the sensor zone and allowed to react for 20 min at room temperature. Following this, 1 mM acetic acid was applied onto the buffer zone as running buffer.

Example 1R. Selectivity and Sensitivity Test of the Paper Biosensor Device (see FIGS. 4b and FIG. 4c).

For the selectivity and sensitivity tests, spiked stool samples with each type of bacteria or with different concentrations of HP were prepared in the same way as described above for the solution-based test. For the selectivity test, 10 µL of stool sample of each of the bacteria culture of ~$10^9$ cfu/mL was mixed with 10 µL of 2× MRB and was applied onto the sensor zone and allowed to react for 20 min at room temperature. Then, 60 µL of 1 mM acetic acid was applied in the buffer zone and allowed to migrate to the detection zone. After 20 min, the color was captured using a cell phone camera and processed using ImageJ software. For the sensitivity test, 10 µL of stool sample spiked with HP at different concentrations (as noted above) was mixed with 10 µL of 2× MRB at room temperature and applied to the sensor zone. After 20 min, 60 µL of 1 mM acetic acid was applied in the buffer zone and allowed to migrate to the detection zone. After 20 min, the color was captured using Samsung Galaxy S3™ and processed by ImageJ and plotted using Microsoft Excel™ software. Tests were run in triplicate to obtain error bars and to calculate a limit of detection based on 3 σ/slope. FIG. 4b shows the results the selectivity test. FIG. 2c shows detection limit for the *Helicobacter pylori* sensor.

Example 1S. Detection Limit with ProFlow™ LFD

Stool samples that were spiked with varying levels of HP were diluted with 2× MRB as noted above and 100 µL of the sample was applied to a ProFlow™ LFD device (Pro-Lab, ON, Canada) following the manufacturer's instructions. Note that ProFlow LFDs required higher sample volume (100 µL) and did not require additional buffer to flow the sample to the detection line. The intensity of the test line was determined by capturing an image with a Samsung Galaxy S3™ and using ImageJ software to provide a color intensity (FIG. 11a and FIG. 11b).

Example 1T. Stability Test of the Paper Biosensor Device

To evaluate the long-term stability of the paper device, a series of paper sensors were prepared and stored at room temperature. At specific time points three paper sensors were used for the detection of HP using CEM-HP prepared from the HP culture containing $10^8$ cfu/mL HP. The color intensity was determined as described above and was evaluated over a period of 4 months of storage at RT (FIG. 12).

Example 1U. Cleavage Test with CEM After Culturing in Tryptic Soya Broth Without Blood To test whether or not the target for the DNAzyme was produced by HP or arose from the sheep's blood used for culturing, HP was cultured in TSB alone for 48 h and 72 h respectively and the CEM was collected as outlined above. Cleavage reactions with these CEMs were carried out individually as follows: 1 μL (2 pmol) of DHp3T4 was dispensed in a microcentrifuge tube followed by sequential addition of 5 μL of 2× SB and 4 μL of CEM. After mixing by pipette, the reaction mixture was incubated at room temperature for 30 min. A negative control was also carried out with reaction buffer (RB) alone without CEM. All reactions were quenched by adding 10 μL of 2× GLB and applied to 10% dPAGE. The results are shown in FIG. 13.

Example 1V. Dehybridization Test with CEM

After the cleavage reaction, a 13 nucleotide (nt) fragment from the 5'-end is produced. To determine if this fragment is released directly from the DNAzyme if or the CEM helps to release it from the DNAzyme, the 13 nt cleaved fragment was hybridized with a fully complementary sequence and incubated with the CEM (40% CEM including 1× SB). A control experiment in the SB alone without CEM was also conducted. The mixtures were analyzed by 8% native PAGE. The results are shown in FIG. 14 (Sequence is shown in Table 5).

Example 1W. Performance of the Paper Biosensor Device with Frozen Faecal Samples To test whether the paper-based DNAzyme biosensor device performs well with both fresh faecal samples and those stored in a frozen state, the color test was conducted with both freshly prepared and frozen/thawed CEM-spiked stool samples containing $10^8$ cfu/mL of HP. The spiked sample was stored at −80° C. for 3 days and then thawed to room temperature, after which the color generation experiment was carried out as described above. The results are shown in FIG. 15.

Example 2. A DNAzyme Probe and Biosensor that Recognizes *Helicobacter pylori*

Specific bacterium-activated RNA-cleaving DNAzymes exist in random-sequence synthetic DNA libraries, and can be isolated using the technique of in vitro selection [8]. These DNAzymes are derived based on their ability to cleave a fluorogenic DNA/RNA substrate at the location of a designated ribonucleotide. The approach does not require a pre-validated biomarker of a bacterium of interest to initiate the DNAzyme selection; instead, the DNAzyme selection and the specificity engineering are done through the use of the crude extracellular mixture (termed CEM for simplicity) of the bacterium as the target in the positive selection step and the CEM from one or more unintended bacteria as the target in the counter selection step [8]. Once the DNAzymes are identified, they can be used to develop simple fluorescent [9] or colorimetric [10] assays to detect this bacterium. Based on these findings, two goals of the current study were: first deriving a highly selective RNA-cleaving DNAzyme for HP and then using it to engineer a sensitive paper device as a simple point of care device capable of achieving colorimetric detection of HP in human stools. Neither of these have been previously demonstrated.

The DNAzyme selection was carried out with a pool of $\sim 10^{14}$ DNA molecules that contained 50 random nucleotides (see FIG. 1a; SEQ ID NO: 21). Specific activation of the DNAzymes by HP was achieved with the use of the CEM of HP (CEM-HP) as the positive selection target and the CEM from the following five bacteria as the counter selection target: *Escherichia coli* O157:H7, *Clostridium difficile*, *Salmonella typhimurium*, *Bacillus subtilis*, *Listeria monocytogenes*. The detailed selection protocol is provided in Example 1E along with a schematic illustration of all the steps involved in each selection cycle (FIG. 5b).

The selection progressed well; by round 12, notable cleavage activity was observed (FIG. 1b). The round-12 DNA pool was subjected to deep sequencing and the top 10 sequences (Table 1, SEQ ID NOs: 1-10) were chemically synthesized and tested for cleavage activity in the presence of CEM-HP, as shown in FIG. 1c. A DNAzyme denoted as DHp3 was found to be the most active DNAzyme. This molecule was further tested when various sequence elements were truncated (FIG. 6a and FIG. 6b). The shortest sequence with full cleavage activity was named DHp3T4 (FIG. 1d) and was used in the remaining experiments.

Inventors next conducted the experiment as shown FIG. 1e to determine if the target that activates DHp3T4 was a protein. When CEM-HP was denatured at 90° C. for 5 minutes (lane 8) or treated with proteinase K (PK; lane 7), it failed to activate the DNAzyme, suggesting that, without wishing to be bound by theory, the target was a protein. Five reactions were conducted to see if the target was simply a ribonuclease. As expected, DHp3T4 was cleaved with purified RNase I from *E. coli* (lane 9); however, the cleavage was not observed with SDS-treated RNase I (lane 10). In contrast, DHp3T4 remained fully active in CEM-HP treated with SDS (lane 4). Moreover, the addition of ribolock (RL, a ribonuclease inhibitor) to CEM-HP did not impact the activity of DHp3T4 (lane 6). In addition, significantly less cleavage product was observed with CEM-HP containing 15 mM EDTA (lane 5), an observation which is not consistent with the fact that many ribonucleases do not require divalent metal ions for function [11]. Finally, inventors tested CEM treated with RNase I followed by addition of ribolock (RNase inhibitor, lane 11), or with DNase I followed by SDS to inhibit DNaseI (lane 12), with cleavage bands observed in both cases. Taken together, without wishing to be bound by theory, these tests strongly suggest that the DNAzyme-activating target was not a RNA or DNA strand, or a ribonuclease.

The molecular weight of the putative protein target was estimated to be between 50-100 KDa, a conclusion drawn from the results shown in FIG. 1f in which CEM-HP was fractionated with molecular weight sizing columns of 30, 50 and 100 kDa. The filtrate of the 100K column (but not 30K and 50K columns) activated the DNAzyme. Further work involving a pull-down assay coupled to mass spectrometry will be needed to conclusively identify the specific target, and will be reported in future work.

The high specificity of DHp3T4 was demonstrated by the experiment shown in FIG. 1g where the DNAzyme was incubated with CEM-HP as well as CEM samples prepared from several control bacteria.

DHp3T4 was expected to produce high-levels of fluorescence upon CEM-HP mediated cleavage because the cleavage reaction occurs at the RNA location sandwiched between a pair of thymidines modified with the FAM fluorophore and the dabcyl quencher (see the reaction scheme shown at the top of FIG. 2). The fluorescence emission of this DNAzyme in response to different concentrations of HP was examined, and data in FIG. 2 shows that the DNAzyme is capable of producing a detectable signal at a concentration as low as $10^4$ cfu/mL. This level of sensitivity is substantially better than the $10^7$ cfu/mL LOD obtained with antibody based lateral flow or dipstick devices [7].

With the confirmed specificity and excellent detection sensitivity associated with DHp3T4, inventors turned attention to the design of a colorimetric sensing system that can be used to engineer a simple and effective paper biosensor device. To engineer such a device, three key factors were considered: 1) a convenient way to immobilize the DNAzyme onto paper surface; 2) a simple but reliable color generation mechanism on paper; 3) minimal signal production due to non-specific interactions from human stool (which represents a very complex biological matrix). The platform described herein was based on two key components: agarose beads for DNAzyme immobilization and urease for signal generation. Agarose beads are widely available, cost-effective, and exhibit very low nonspecific binding to DNA and proteins [12], which is important given the complexity of the sample matrix. Urease was chosen for colorimetric signal production simply because, as inventors have demonstrated previously, urease can be used to set up a very simple, litmus test-like assay in which it hydrolyzes urea into ammonia, resulting in a change in pH that can be expediently detected using vibrant pH indicators [10a].

Inventors first assessed the proposed colorimetric test in solution using agarose beads conjugated with DHp3T4 tagged with urease (FIG. 3a). Briefly, the DNAzyme was biotinylated at its 3'-end so that it could be immobilized onto streptavidin-coated agarose beads. The DNAzyme was also modified at the 5'-end with a DNA tag so that it could hybridize to the adapter DNA conjugated to urease. The DNAzyme molecules in the as-assembled beads are expected to undergo the cleavage reaction, releasing the cleavage fragment containing urease. The freed urease is separated from uncleaved urease by centrifugation, and then added to a phenol red solution to report the increase of pH produced by the hydrolysis of urea via a color change.

The proposed assay worked very well in preliminary test as it was indeed capable of producing a vibrant yellow-to-red color change (from the image on the left to the image on the right) in the presence of CEM-HP or a stool sample containing HP (FIG. 7a and FIG. 7b). Based on the results, inventros examined the full functionality of the assay in human stool samples spiked with HP or one of the control bacteria. As shown in FIG. 3b, only the HP-spiked stool sample resulted in the expected color change in a time-dependent fashion. Inventors also investigated the sensitivity of the colorimetric assay using stool samples spiked with different concentrations of HP ($0$-$10^8$ cfu/mL). The results indicated that the solution-based assay was capable of detecting as low as $10^4$ cfu/mL HP in real human stools (FIG. 3c). Interestingly, this level of detection sensitivity is identical to the fluorescence assay (FIG. 2), even though the reaction time was half that of the fluorescence assay (45 min vs 80 min). This demonstrates that incorporation of the urease catalyzed reaction resulted in amplification to allow the colorimetric assay to achieve an LOD at least as good as that of the fluorescence system.

Example 3. A Biosensor Device for Detecting *Helicobacter pylori* Based on DNAzymes and Paper Substrate Finally, inventors turned attention to the design and validation of a simple paper biosensor device that employs the DNAzyme-urease-beads assembly, as illustrated in FIG. 4a. It features three zones for different purposes: a middle sensor zone (zone 2) that contains sensing beads, the right detection zone (zone 3) where urea and phenol red are placed, and a left buffer zone (zone 1) where a running buffer is added to initiate the lateral flow process after the cleavage reaction. The device was produced on a plastic-backed HF180 nitrocellulose membrane, using wax printing for creating the aforementioned 3 zones interconnected by a channel and surrounded by hydrophobic barriers The DNAzyme/urease/beads assembly and the urea/phenol red mixture were immobilized in their respective zones through formation of a reagent film with pullulan. There are two reasons for the use of the pullulan films. First, as inventors have shown previously, pullulan film formation provides long-term stability to entrapped macromolecules including protein enzymes and RNA-containing nucleic acids [13]. The second reason was based on observation that the addition of the mixture to the sensor zone caused significant capillary-driven flow toward the other two zones (see the liquid flow using a model dye solution in FIG. 8a). The use of a film formed with 5 wt % pullulan easily overcame this unwanted flow action owing to the increased viscosity (FIG. 8b). This is particularly important for the sensor zone as the applied test sample would have to remain in place for some time in order to have sufficient time to contact the DNAzyme molecules on beads and let them cleave.

In a typical test, a sample (10 μL) was mixed with an equivalent volume of 2× reaction buffer and the resultant 20 μL sample was added to the sensor zone and incubated for 20 min to allow the DNAzyme to cleave. Next, 60 μL of running buffer was applied in the buffer zone, which flows through the sensor zone to carry the released urease into the detection zone while leaving the beads in the sensor zone owing to their large size (~100 μm diameter). Inventors tested different running buffers and found that 1 mM acetic acid worked best (FIG. 9a and FIG. 9b).

The selectivity of the biosensor device was evaluated with stool samples spiked with $10^8$ cfu/mL of various bacteria and the results in FIG. 4b indicate that the device provided excellent selectivity. To ensure that the signal originated only from urease that was released from DNAzymes, rather than endogenous urease present in bacteria, $10^7$ cfu/mL of HP, KP or PA was added [14] to sensors with no DNAzyme present on the sensor zone. None of these provided a color change (FIG. 10), confirming that the signal arose only from urease released from the DNAzyme.

The sensitivity of the biosensor device was then assessed with stool samples containing varying concentrations of HP spanning the clinically relevant range ($10^3$-$10^6$ cfu/mL of fecal matter as determined by PCR) [15], followed by cell phone imaging and data processing using ImageJ software (FIG. 4c). This analysis resulted in an estimated limit of detection (LOD; 3s) of $10^4$ cfu/mL, similar to the solution based assay. As a comparison, the same samples were applied to a commercially available antibody-based lateral flow device (LFD), which exhibited the expected higher detection limit of ca. $10^7$ cfu/mL (FIG. 11a and FIG. 11b) [7].

Inventors also investigated the stability of the biosensor device. A group of devices were stored at room temperature (23±1° C.) in the dark and tested for functionality over a period of 4 months (FIG. 12). The devices remained fully active during the entire testing period, consistent with previous findings on the stability of bioreagents entrapped in pullulan [9b, 11]. The paper devices should therefore be sufficiently stable to allow shipping, storage and use in resource limited regions, where refrigeration may not be available.

In summary, inventors have isolated DNAzyme probes for *H. pylori* by in vitro selection and developed an effective beads-based colorimetric assay that can detect HP either in solution or on a paper biosensor device. In both cases the assay performs robustly even with stool samples. The paper device can provide a semi-quantitative test for *H. pylori* in less than an hour in a non-invasive manner. It is portable and simple to use, stable at room temperature for at least 4 months, and capable of generating a colorimetric readout that can be analyzed without sophisticated equipment. Inventors believe this work represents a significant step forward towards developing low-cost, portable, point-of-care diagnostics using DNAzyme probes for detecting pathogenic bacteria in clinical settings, especially in resource limited areas.

While the present disclosure has been described with reference to examples, it is to be understood that the scope of the claims should not be limited by the embodiments set forth in the examples, but should be given the broadest interpretation consistent with the description as a whole.

All publications, patents and patent disclosures are herein incorporated by reference in their entirety to the same extent as if each individual publication, patent or patent disclosure was specifically and individually indicated to be incorporated by reference in its entirety. Where a term in the present disclosure is found to be defined differently in a document incorporated herein by reference, the definition provided herein is to serve as the definition for the term.

TABLE 1

| Identifier | Name of nucleic acid | Sequence (5'-3') | Round-12 Screening Abundance |
|---|---|---|---|
| SEQ ID NO: 1 | DHp01 | ATGCCATCCTACCAACCCCCGGTAACGGCTAGATGGG TATTGGTTAGTGTGGGCCCGTGTTGGAGCTCTGAACT CG | 29777 |
| SEQ ID NO: 2 | DHp02 | ATGCCATCCTACCAACCCAGGGTAAGGTATAACAATG GTAGACAGGTGTGTGGTCCGGGTGCTGAGCTCTGAAC TCG | 15608 |
| SEQ ID NO: 3 | DHp03 | ATGCCATCCTACCAACCCATGTGGTTTGTTGAGATGG TCTTTGGTATGTGGGGTCCGAGGGTAGAGCTCTGAAC TCG | 15378 |
| SEQ ID NO: 4 | DHp04 | ATGCCATCCTACCAACACACGGAGCAGGTGGAGTTGC ATCTGGATAGGGGGTCGCCGGGTATAGAGCTCTGAAC TCG | 13082 |
| SEQ ID NO: 5 | DHp05 | ATGCCATCCTACCAACACCCCAGGTCGTTTGAAGTAC CTCTTGGGAATGTGGTCACCGATGTTGGAGCTCTGAA CTCG | 8441 |
| SEQ ID NO: 6 | DHp06 | ATGCCATCCTACCAACCCCAAGTACGGTTGCGCATGG TAAATATGTGGTGTGGTCCCGATGTAGAGCTCTGAAC TCG | 6901 |
| SEQ ID NO: 7 | DHp07 | ATGCCATCCTACCAACCACAGGATTGCGTGGATTCTT CATAATGGTGGTGAGGTCGAGGGTTGGAGCTCTGAAC TCG | 6716 |
| SEQ ID NO: 8 | DHp08 | ATGCCATCCTACCAACCCGACAGGGACTGGTTGCCAC GGGAGCTGTGTAAGAGGGCCGTGTTATGAGCTCTGAA CTCG | 6256 |
| SEQ ID NO: 9 | DHp09 | ATGCCATCCTACCAACCAACGGAAAGGTGGTCGATTT CTAGGACTATTGAGGTCATCCGTGGTGGAGCTCTGAA CTCG | 6193 |
| SEQ ID NO: 10 | DHp010 | ATGCCATCCTACCAACCACCCGGTTAGACGGAAGTGG GCTATTGTGTATTGGGTCGCGATGAGGAGCTCTGAAC TCG | 5783 |
| SEQ ID NO: 11 | DHp3T1 | ATGCCATCCTACCAACCCATGTGGTTTGTTGAGATGG TCTTTGGTATGTGGGGTCCGAGGGTA | |
| SEQ ID NO: 12 | DHp3T2 | CCATGTGGTTTGTTGAGATGGTCTTTGGTATGTGGGG TCCGAGGGTAGAGCTCTGAACTCG | |
| SEQ ID NO: 13 | DHp3T3 | CCATGTGGTTTGTTGAGATGGTCTTTGGTATGTGGGG TCCGAGGGTA | |

TABLE 1-continued

| Identifier | Name of nucleic acid | Sequence (5'-3') | Round-12 Screening Abundance |
|---|---|---|---|
| SEQ ID NO: 14 | DHp3T4 | ATGCCATCGATGGTCTTTGGTATGTGGGGTCCGAGGG TAGAGCTCTGAACTCG | |
| SEQ ID NO: 15 | DHp3T4M | ATGCCATCGATGGTCTTTGGTATGTGGGGTC*gacg*GG TAGAGCTCTGAACTCG | |

The random region in each of DHp01-DHp10 is shown in bold.
Italic small letters in DHp3T4M represent the base mutations

TABLE 2

Sequences of FIG. 1 and FIG. 5

| Identifier | Name of nucleic acid | Sequence (5'-3') |
|---|---|---|
| SEQ ID NO: 16 | AdDNA | CACTCTACCT ACTCCATCAT TTTTTTTTT |
| SEQ ID NO: 17 | FS2 | TGATGGAGTA GGTAGAGTGT TTTTACGTGC CTGATGGATC CTATGAACTG ACQRFGACCT CACTACCAAG |
| SEQ ID NO: 18 | BDHp3T4 | ATGCCATCGA TGGTCTTTGG TATGTGGGGT CCGAGGGTAG AGCTCTGAAC TCGTTTTTTT TTTB |
| SEQ ID NO: 19 | LT | GTTGGTAGGA TGGCATCTTG GTAGTGAGGT C |
| SEQ ID NO: 20 | B-DHp3T4-FS2 | TGATGGAGTA GGTAGAGTGT TTTTACGTGC CTGATGGATC CTATGAACTG ACQRFGACCT CACTACCAAG ATGCCATCGA TGGTCTTTGG TATGTGGGGT CCGAGGGTAG AGCTCTGAAC TCGTTTTTTT TTTB |
| SEQ ID NO: 21 | DNA library | CTATGAACTG ACQRFGACCT CACTACCAAG ATGCCATCCT ACCAACNNNN NNNNNNNNNN NNNNNNNNNN NNNNNNNNNN NNNNNNNNNN NNNNNNGAGC TCTGAACTCG |
| SEQ ID NO: 22 | DNA library middle | ATGCCATCCT ACCAACNNNN NNNNNNNNNN NNNNNNNNNN NNNNNNNNNN NNNNNNNNNN NNNNNNGAGC TCTGAACTCG |
| SEQ ID NO: 23 | FP | ATGCCATCCTACCAAC |
| SEQ ID NO: 24 | RP1 | CGAGTTCAGAGCTC |
| SEQ ID NO: 25 - L- SEQ ID NO: 71 | RP2 | AAAAAAAAAA AAAAAAAAAA L CGAGTTCAGAGCTC |
| SEQ ID NO: 26 | FS | CTATGAACTG ACQRFGACCT CACTACCAAG |
| SEQ ID NO: 27 | FS-DHp3T4 | CTATGAACTG ACQRFGACCT CACTACCAAG ATGCCATCGATGGTCTTTGGTATGTGGGGTCC GAGGGTAGAGCTCTGAACTCG |

Notation:
Q: dabcyl-dT,
R: adenine ribonucleotide,
F: Fluorescein-dT,
L: glycol linker,
N: random nucleotide

TABLE 3

Sequences of random region

| Identifier | Random Region ID | Sequence of random region (5'→3') |
|---|---|---|
| SEQ ID NO: 28 | RR-DHp01 | CCCCGGTAACGGCTAGATGGGTATTGGTTAGTGTGGGCCCGTGTTG |
| SEQ ID NO: 29 | RR-DHp02 | CCAGGGTAAGGTATAACAATGGTAGACAGGTGTGTGGTCCGGGTGCT |
| SEQ ID NO: 30 | RR-DHp04 | ACACGGAGCAGGTGGAGTTGCATCTGGATAGGGGGTCGCCGGGTATA |
| SEQ ID NO: 31 | RR-DHp05 | ACCCCAGGTCGTTTGAAGTACCTCTTGGGAATGTGGTCACCGATGTTG |
| SEQ ID NO: 32 | RR-DHp06 | CCCAAGTACGGTTGCGCATGGTAAATATGTGGTGTGGTCCCGATGTA |
| SEQ ID NO: 33 | RR-DHp07 | CACAGGATTGCGTGGATTCTTCATAATGGTGGTGAGGTCGAGGGTTG |
| SEQ ID NO: 34 | RR-DHp09 | CCGACAGGGACTGGTTGCCACGGGAGCTGTGTAAGAGGGCCGTGTTAT |
| SEQ ID NO: 35 | RR-DHp09 | CAACGGAAAGGTGGTCGATTTCTAGGACTATTGAGGTCATCCGTGGTG |
| SEQ ID NO: 36 | RR-DHp10 | CACCCGGTTAGACGGAAGTGGGCTATTGTGTATTGGGTCGCGATGAG |

TABLE 4

Sequences of flanking random region.

| Identifier | Terminus | Sequence surrounding random region |
|---|---|---|
| SEQ ID NO: 37 | 5' | ATGCCATCCTACCAAC |
| SEQ ID NO: 38 | 5' | TGCCATCCTACCAAC |
| SEQ ID NO: 39 | 5' | GCCATCCTACCAAC |
| SEQ ID NO: 40 | 5' | CCATCCTACCAAC |
| SEQ ID NO: 41 | 5' | CATCCTACCAAC |
| SEQ ID NO: 42 | 5' | ATCCTACCAAC |
| SEQ ID NO: 43 | 5' | TCCTACCAAC |
| SEQ ID NO: 44 | 5' | CCTACCAAC |
| SEQ ID NO: 45 | 5' | CTACCAAC |
| SEQ ID NO: 46 | 5' | TACCAAC |
| SEQ ID NO: 47 | 5' | ACCAAC |
| SEQ ID NO: 48 | 5' | CCAAC |
| SEQ ID NO: 49 | 5' | CAAC |
| SEQ ID NO: 50 | 5' | AAC |
| SEQ ID NO: 51 | 5' | AC |
| SEQ ID NO: 52 | 5' | C |
| SEQ ID NO: 53 | 3' | GAGCTCTGAACTCG |
| SEQ ID NO: 54 | 3' | GAGCTCTGAACTC |
| SEQ ID NO: 55 | 3' | GAGCTCTGAACT |
| SEQ ID NO: 56 | 3' | GAGCTCTGAAC |
| SEQ ID NO: 57 | 3' | GAGCTCTGAA |
| SEQ ID NO: 58 | 3' | GAGCTCTGA |
| SEQ ID NO: 59 | 3' | GAGCTCTG |
| SEQ ID NO: 60 | 3' | GAGCTCT |
| SEQ ID NO: 61 | 3' | GAGCTC |
| SEQ ID NO: 62 | 3' | GAGCT |
| SEQ ID NO: 63 | 3' | GAGC |
| SEQ ID NO: 64 | 3' | GAG |
| SEQ ID NO: 65 | 3' | GA |
| SEQ ID NO: 66 | 3' | G |

TABLE 5

Sequences of FIG. 14

| Identifier | Name of nucleic acid | Sequence (5'-3') |
|---|---|---|
| SEQ ID NO: 67 | RB + CEM 5' | CTATGAACTGACF |
| SEQ ID NO: 68 | RB + CEM 3' | GATACTTGACTGA |

TABLE 5-continued

Sequences of FIG. 14

| Identifier | Name of nucleic acid | Sequence (5'-3') |
|---|---|---|
| SEQ ID NO: 69 | RB + CEM 5' inverse | AGTCAGTTCATAG |
| SEQ ID NO: 70 | Marker | CTATGAACTGACF |

Notation:
F: Fluorescein

FULL CITATIONS FOR DOCUMENTS REFERRED TO IN THE DISCLOSURE

[1] a) P. N. Fonkwo, *EMBO Rep.*, 2008, S13-17; b) M. Suhrcke, D. Stuckler, J. E. Suk, M. Desai, M. Senek, M. McKee, S. Tsolova, S. Basu, I. Abubakar, P. Hunter, B. Rechel, J. C. Semenza, *PLoS One.* 2011, 6, e20724

[2] a) N. Uemura, S. Okamoto, S. Yamamoto, N. Matsumura, S. Yamaguchi, M. Yamakido, K. Taniyama, N. Sasaki, R. J. Schlemper, *N. Eng. J. Med.*, 2001, 345, 784-789; b) J. Khatoon, R. P. Rai, K. N. Prasad, *World J Gastrointest. Oncol.*, 2016, 8, 147-158.

[3] a) X. Calvet, *Gastroenterol. Clin. North Am.*, 2015, 44, 507-518; b) M. De Falco, A. Lucariello, S. Iaquinto, V. Esposito, G. Guerra, A. De Luca, *J. Cell Physiol.*, 2015, 230, 1702-1707; c) J. Jiang, Y. Chen, J. Shi, C. Song, J. Zhang, K. Wang, *Eur. J. Clin. Microbiol. Infect. Dis.*, 2016, 36, 199-212.

[4] a) A. T. B. Abadi. *Front. Med. (Lausanne).* 2014, 1, 34; b) R. Ghotaslou, H. E. Leylabadlo, Y. M. Asl. *World J. Methodol.*, 2015, 5, 164-174.

[5] S. Backert, M. Neddermann, G. Maubach, M. Naumann. *Helicobacter*, 2016, 21, 19-25.

[6] a) M. Ferwana, I. Abdulmajeed, A. Alhajiahmed, W. Madani, B. Firwana, R. Hasan, O. Altayar, P. J. Limburg, M. H. Murad, B. Knawy. *World J. Gastroenterol.*, 2015, 21, 1305-1314; b) C. R. Carlini, R. Ligabue-Braun. *Toxicon.*, 2016, 110, 90-109.

[7] a) H. Boutal, T. Naas, K. Devilliers, S. Oueslati, L. Dortet, S. Bernabeu, S. Simon, H. Volland. *J Clin Microbiol.* 2017, 55, 2018-2029, b) E. J. Scharinger, R. Dietrich, T. Wittwer, E. Märtlbauer, K. Schauer, *Front Microbiol.* 2017, 8, 1826.

[8] a) M. M. Ali, S. D. Aguirre, H. Lazim, Y. Li. *Angew. Chem. Int. Ed. Engl.*, 2011, 50, 3751-3754; b) Z. Shen, Z. Wu, D. Chang, W. Zhang, K. Tram, C. Lee, P. Kim, B. J. Salena, Y. Li, *Angew. Chem. Int. Ed. Engl.*, 2016, 55, 2431-2434.

[9] a) S. D. Aguirre, M. M. Ali, B. J. Salena, Y. Li, *Biomolecules,* 2013, 3, 563-577; b) M. M. Ali, C. L. Brown, S. Jahanshahi-Anbuhi, Y. Li, J.D. Brennan, *Scientific Reports,* 2017, 7, 12335.

[10] a) K. Tram, P. Kanda, B.J. Salena, S. Huan, Y. Li, *Angew. Chem. Int. Ed. Engl.*, 2014, 53, 12799-12802; b) D. Mazumdar, J. Liu, G. Lu, J. Zhou, Y. Lu, *Chem. Commun.*, 2010, 46, 1416-1418; c) Z. Fang, J. Huang, P. Lie, Z. Xiao, C. Ouyang, Q. Wu, Y. Wu, G. Liu, L. Zeng, *Chem. Commun.*, 2010, 46, 9043-9045; d) J. Liu, D. Mazumdar, Y. Lu, *Angew. Chem. Int. Ed. Engl.*, 2006, 45, 7955-7959.

[11] a) C. J. Vincent, K. David, *Eur. J Biochem.*, 1989, 181, 363-370; b) D. Giuseppe, F. R. James, Ribonucleases: Structures and Functions, Academic press, 1996

[12] a) B. Vogelstein, D. Gillespie, *Proc. Natl. Acad. Sci. USA,* 1979, 76, 615-619; b) H. Zheng, Y. Lang, J. Yu, Z. Han, B. Chen, Y. Wang, *Colloids Surf B Biointerfaces,* 2019, 178, 80-86

[13] a) S. Jahanshahi-Anbuhi, K. Pennings, V. Leung, M. Liu, C. Carrasquilla, B. Kannan, Y. Li, R. Pelton, J. D. Brennan, C. D. Filipe. *Angew. Chem. Int. Ed. Engl.*, 2014, 53, 6155-6158; b) P. Y. Hsieh, M. M. Ali, K. Tram, S. Jahanshahi-Anbuhi, C. Brown, J. D. Brennan, C. D. Filipe, Y. Li, *ChemBioChem,* 2017, 18, 502-505; c) M. Liu, C. Y. Hui, Q. Zhang, J. Gu, B. Kannan, S. Jahanshahi-Anbuhi, C. D. Filipe, J. D. Brennan, Y. Li, *Angew. Chem. Int. Ed. Engl.*, 2016, 55, 2709-2713.

[14] a) I. Konieczna, P. Zarnowiec, M. Kwinkowski, B. Kolesinska, J. Fraczyk, Z. Kaminski, W. Kaca, *Curr Protein Pept Sci,* 2012, 13, 789-806; b) D. Mora, S. Arioli, *PLoS Pathog.* 2014, 10, e1004472; c) R. S. Bradbury, D. W. Reid, A. C. Champion, *Br J Biomed Sci,* 2014, 71, 175-177.

[15] A. Makristathis, E. Pasching, K. Schütze, M. Wimmer, M. L. Rotter, A. M. Hirschl. *J Clin Microbiol.* 1998, 36, 2772-2774.

The invention claimed is:

1. A lateral flow biosensor device for detecting the presence of an analyte in a test sample, comprising:
   i) a buffer zone for applying a running buffer, the buffer zone being connected through a flow channel to ii) a sensor zone for applying a test sample comprising an immobilized biosensor entrapped by a stabilizing matrix, the sensor zone being connected through a flow channel to iii) a detection zone for indicating the presence or a range of levels of the analyte,
   wherein the immobilized biosensor in the sensor zone is immobilized to a solid support, and the immobilized biosensor comprises:
      a) a sensor nucleic acid molecule comprising a first region comprising a nucleic acid-cleaving catalytic nucleic acid probe specific to the analyte, and a second region comprising a nucleic acid sequence having a linkage substrate and a releasable tag nucleic acid molecule, and
      b) a reporter conjugated to the releasable tag nucleic acid molecule of the sensor nucleic acid molecule or an adapter nucleic acid molecule conjugated with a reporter,
   wherein the adapter nucleic acid molecule comprises a nucleic acid sequence complementary to the releasable tag nucleic acid molecule or a portion thereof, or sufficient complementarity that provides a strong enough interaction to prevent dehybridization,
   wherein the adapter nucleic acid molecule hybridizes to the releasable tag nucleic acid fragment to form a releasable fragment comprising the reporter,
   wherein, in the presence of analyte, the nucleic acid-cleaving catalytic nucleic acid probe is activated and cleaves the linkage substrate at a cleavage site, thereby releasing the releasable tag nucleic acid molecule conjugated with the reporter, or the releasable fragment comprising the reporter, and
   wherein, upon cleavage, the releasable tag nucleic acid molecule conjugated with the reporter, or the releasable fragment conjugated with the reporter migrates to the detection zone due to lateral flow of the running buffer to produce a signal.

2. The lateral flow biosensor device of claim 1, wherein the reporter is a reporter enzyme or a gold nanoparticle.

3. The lateral flow biosensor device of claim 2, wherein the reporter is a reporter enzyme and the detection zone comprises a reporting solution entrapped by the stabilizing matrix.

4. The lateral flow biosensor device of claim 1, wherein the solid support comprises agarose beads, optionally the biosensor is immobilized to the agarose beads by biotin-streptavidin interaction.

5. The lateral flow biosensor device of claim 1, wherein the analyte is a protein.

6. The lateral flow biosensor device of claim 1, wherein the stabilizing matrix is oxygen impermeable, has a viscosity of between 10-50 centipoise, and provides stability to the immobilized biosensor in the sensor zone and the reporting solution in the detection zone for at least four months, optionally the stabilizing matrix comprises pullulan.

7. The lateral flow biosensor device of claim 1, wherein the lateral flow biosensor device comprises nitrocellulose paper, a polymer support layer and a hydrophobic material.

8. The lateral flow biosensor device of claim 1, wherein the linkage substrate comprises a ribonucleotide linkage substrate.

9. The lateral flow biosensor device of claim 1, wherein the nucleic acid-cleaving catalytic nucleic acid probe comprises a DNAzyme, optionally the DNAzyme comprises a sequence of any one of SEQ ID NO: 1-14 or 28-36, or a functional fragment or modified derivative thereof.

10. The lateral flow biosensor device of claim 1, wherein the reporter enzyme is urease, alkaline phosphatase, cholinesterase, or horseradish peroxidase.

11. The lateral flow biosensor device of claim 10, wherein the reporter enzyme is urease and the reporting solution comprises urea and a pH sensitive dye, optionally phenol red, bromothymol blue, 6,8-dinitro-2,4-(1H)quinazolinedione, brilliant yellow, neutral red, m-nitrophenol, cresol red, naphtholphthalein, phenolphthalein, m-cresol purple, or o-cresolphthalein complexone.

12. The lateral flow biosensor device of claim 1, wherein the running buffer comprises acetic acid, optionally 1 mM acetic acid.

13. The lateral flow biosensor device of claim 1, wherein the analyte comprises a molecule, compound or substance that is present in or on a microorganism, or is generated, excreted, secreted or metabolized by a microorganism.

14. The lateral flow biosensor device of claim 13, wherein the microorganism is *Helicobacter pylori, Escherichia coli* O157:H7, *Clostridium difficile, Salmonella serovar typhimurium, Listeria monocytogenes, Klebsiella pneumoniae, Fusobacterium nucleatum, Pseudomonas aeruginosa, Bacteroides fragilis, Enterococcus faecium* or *Streptococcus salivarius*.

15. A kit for detecting a microorganism, wherein the kit comprises the lateral flow biosensor device in claim 1, one or more components required thereof, and instructions for use of the kit for detecting the microorganism.

16. A method of detecting a microorganism in a test sample, comprising:
    applying the test sample to the sensor zone of the lateral flow biosensor device in claim 1,
        wherein the test sample comprises an analyte from a microorganism, and
        wherein the analyte contacts the immobilized biosensor in the sensor zone and activates the nucleic acid-cleaving nucleic acid probe which cleaves the linkage substrate at a cleavage site and releases a fragment comprising the reporter,
    applying a running buffer to the buffer zone of the lateral flow biosensor device, whereby the running buffer laterally flows into the sensor zone and the released fragment comprising the reporter then moves laterally to the detection zone,
    allowing the reporter to produce a signal, and
    detecting the signal in the detection zone, optionally the signal is a color change signal, optionally color is indicative of amount of analyte.

17. The method of claim 16, wherein the reporter is a reporter enzyme or a gold nanoparticle, optionally the reporter enzyme is urease, alkaline phosphatase, cholinesterase, or horseradish peroxidase.

* * * * *

SEQUENCE LISTING

```
<160> NUMBER OF SEQ ID NOS: 71

<210> SEQ ID NO 1
<211> LENGTH: 76
<212> TYPE: DNA
<213> ORGANISM: Artificial Sequence
<220> FEATURE:
<223> OTHER INFORMATION: Synthetic construct

<400> SEQUENCE: 1
atgccatcct accaacccc ggtaacggct agatgggtat tggttagtgt gggcccgtgt      60
tggagctctg aactcg                                                     76

<210> SEQ ID NO 2
<211> LENGTH: 77
<212> TYPE: DNA
<213> ORGANISM: Artificial Sequence
<220> FEATURE:
```

<223> OTHER INFORMATION: Synthetic construct

<400> SEQUENCE: 2
atgccatcct accaacccag ggtaaggtat aacaatggta gacaggtgtg tggtccgggt    60
gctgagctct gaactcg                                                   77

<210> SEQ ID NO 3
<211> LENGTH: 77
<212> TYPE: DNA
<213> ORGANISM: Artificial Sequence
<220> FEATURE:
<223> OTHER INFORMATION: Synthetic construct

<400> SEQUENCE: 3
atgccatcct accaacccat gtggtttgtt gagatggtct ttggtatgtg gggtccgagg    60
gtagagctct gaactcg                                                   77

<210> SEQ ID NO 4
<211> LENGTH: 77
<212> TYPE: DNA
<213> ORGANISM: Artificial Sequence
<220> FEATURE:
<223> OTHER INFORMATION: Synthetic construct

<400> SEQUENCE: 4
atgccatcct accaacacac ggagcaggtg gagttgcatc tggatagggg gtcgccgggt    60
atagagctct gaactcg                                                   77

<210> SEQ ID NO 5
<211> LENGTH: 78
<212> TYPE: DNA
<213> ORGANISM: Artificial Sequence
<220> FEATURE:
<223> OTHER INFORMATION: Synthetic construct

<400> SEQUENCE: 5
atgccatcct accaacaccc caggtcgttt gaagtacctc ttgggaatgt ggtcaccgat    60
gttggagctc tgaactcg                                                  78

<210> SEQ ID NO 6
<211> LENGTH: 77
<212> TYPE: DNA
<213> ORGANISM: Artificial Sequence
<220> FEATURE:
<223> OTHER INFORMATION: Synthetic construct

<400> SEQUENCE: 6
atgccatcct accaacccca agtacggttg cgcatggtaa atatgtggtg tggtcccgat    60
gtagagctct gaactcg                                                   77

<210> SEQ ID NO 7
<211> LENGTH: 77
<212> TYPE: DNA
<213> ORGANISM: Artificial Sequence
<220> FEATURE:
<223> OTHER INFORMATION: Synthetic construct

<400> SEQUENCE: 7
atgccatcct accaaccaca ggattgcgtg gattcttcat aatggtggtg aggtcgaggg    60
ttggagctct gaactcg                                                   77

```
<210> SEQ ID NO 8
<211> LENGTH: 78
<212> TYPE: DNA
<213> ORGANISM: Artificial Sequence
<220> FEATURE:
<223> OTHER INFORMATION: Synthetic construct

<400> SEQUENCE: 8
atgccatcct accaacccga cagggactgg ttgccacggg agctgtgtaa gagggccgtg      60
ttatgagctc tgaactcg                                                   78

<210> SEQ ID NO 9
<211> LENGTH: 78
<212> TYPE: DNA
<213> ORGANISM: Artificial Sequence
<220> FEATURE:
<223> OTHER INFORMATION: Synthetic construct

<400> SEQUENCE: 9
atgccatcct accaaccaac ggaaaggtgg tcgatttcta ggactattga ggtcatccgt      60
ggtggagctc tgaactcg                                                   78

<210> SEQ ID NO 10
<211> LENGTH: 77
<212> TYPE: DNA
<213> ORGANISM: Artificial Sequence
<220> FEATURE:
<223> OTHER INFORMATION: Synthetic construct

<400> SEQUENCE: 10
atgccatcct accaaccacc cggttagacg aagtgggct attgtgtatt gggtcgcgat       60
gaggagctct gaactcg                                                    77

<210> SEQ ID NO 11
<211> LENGTH: 63
<212> TYPE: DNA
<213> ORGANISM: Artificial Sequence
<220> FEATURE:
<223> OTHER INFORMATION: Synthetic construct

<400> SEQUENCE: 11
atgccatcct accaacccat gtggtttgtt gagatggtct ttggtatgtg gggtccgagg      60
gta                                                                   63

<210> SEQ ID NO 12
<211> LENGTH: 61
<212> TYPE: DNA
<213> ORGANISM: Artificial Sequence
<220> FEATURE:
<223> OTHER INFORMATION: Synthetic construct

<400> SEQUENCE: 12
ccatgtggtt tgttgagatg gtctttggta tgtggggtcc gagggtagag ctctgaactc      60
g                                                                     61

<210> SEQ ID NO 13
<211> LENGTH: 47
<212> TYPE: DNA
<213> ORGANISM: Artificial Sequence
<220> FEATURE:
<223> OTHER INFORMATION: Synthetic construct

<400> SEQUENCE: 13
```
ccatgtggtt tgttgagatg gtctttggta tgtggggtcc gagggta                    47

<210> SEQ ID NO 14
<211> LENGTH: 53
<212> TYPE: DNA
<213> ORGANISM: Artificial Sequence
<220> FEATURE:
<223> OTHER INFORMATION: Synthetic construct

<400> SEQUENCE: 14
atgccatcga tggtctttgg tatgtggggt ccgagggtag agctctgaac tcg            53

<210> SEQ ID NO 15
<211> LENGTH: 53
<212> TYPE: DNA
<213> ORGANISM: Artificial Sequence
<220> FEATURE:
<223> OTHER INFORMATION: Synthetic construct

<400> SEQUENCE: 15
atgccatcga tggtctttgg tatgtggggt cgacgggtag agctctgaac tcg            53

<210> SEQ ID NO 16
<211> LENGTH: 29
<212> TYPE: DNA
<213> ORGANISM: Artificial Sequence
<220> FEATURE:
<223> OTHER INFORMATION: Synthetic construct

<400> SEQUENCE: 16
cactctacct actccatcat ttttttttt                                       29

<210> SEQ ID NO 17
<211> LENGTH: 70
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (53)..(53)
<223> OTHER INFORMATION: n = dabcyl-dt
<220> FEATURE:
<221> NAME/KEY: misc_feature
<222> LOCATION: (55)..(55)
<223> OTHER INFORMATION: n = fluorescein-dt

<400> SEQUENCE: 17
tgatggagta ggtagagtgt ttttacgtgc ctgatggatc ctatgaactg acnrngacct    60
cactaccaag                                                            70

<210> SEQ ID NO 18
<211> LENGTH: 64
<212> TYPE: DNA
<213> ORGANISM: Artificial Sequence
<220> FEATURE:
<223> OTHER INFORMATION: Synthetic construct

<400> SEQUENCE: 18
atgccatcga tggtctttgg tatgtggggt ccgagggtag agctctgaac tcgttttttt    60 tttb                                                                  64

<210> SEQ ID NO 19
<211> LENGTH: 31
<212> TYPE: DNA
<213> ORGANISM: Artificial Sequence

```
<220> FEATURE:
<223> OTHER INFORMATION: Synthetic construct

<400> SEQUENCE: 19
gttggtagga tggcatcttg gtagtgaggt c                              31

<210> SEQ ID NO 20
<211> LENGTH: 134
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (53)..(53)
<223> OTHER INFORMATION: n = dabcyl-dt
<220> FEATURE:
<221> NAME/KEY: misc_feature
<222> LOCATION: (55)..(55)
<223> OTHER INFORMATION: n = fluorescein-dt

<400> SEQUENCE: 20
tgatggagta ggtagagtgt ttttacgtgc ctgatggatc ctatgaactg acnrngacct    60
cactaccaag atgccatcga tggtctttgg tatgtggggt ccgagggtag agctctgaac   120
tcgttttttt tttb                                                    134

<210> SEQ ID NO 21
<211> LENGTH: 110
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(13)
<223> OTHER INFORMATION: n = dabcyl-dt
<220> FEATURE:
<221> NAME/KEY: misc_feature
<222> LOCATION: (15)..(15)
<223> OTHER INFORMATION: n = fluorescein-dt
<220> FEATURE:
<221> NAME/KEY: misc_feature
<222> LOCATION: (47)..(96)
<223> OTHER INFORMATION: n is a, c, g, or t

<400> SEQUENCE: 21
ctatgaactg acnrngacct cactaccaag atgccatcct accaacnnnn nnnnnnnnn     60 nnnnnnnnnn nnnnnnnnnn nnnnnnnnnn nnnnnngagc tctgaactcg              110

<210> SEQ ID NO 22
<211> LENGTH: 80
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (17)..(66)
<223> OTHER INFORMATION: n is a, c, g, or t

<400> SEQUENCE: 22
atgccatcct accaacnnnn nnnnnnnnnn nnnnnnnnnn nnnnnnnnnn nnnnnnnnnn    60
nnnnnngagc tctgaactcg                                                80

<210> SEQ ID NO 23
<211> LENGTH: 16
<212> TYPE: DNA
```

```
<213> ORGANISM: Artificial Sequence
<220> FEATURE:
<223> OTHER INFORMATION: Synthetic construct

<400> SEQUENCE: 23
atgccatcct accaac                                                        16

<210> SEQ ID NO 24
<211> LENGTH: 14
<212> TYPE: DNA
<213> ORGANISM: Artificial Sequence
<220> FEATURE:
<223> OTHER INFORMATION: Synthetic construct

<400> SEQUENCE: 24
cgagttcaga gctc                                                          14

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
aaaaaaaaaa aaaaaaaaaa                                                    20

<210> SEQ ID NO 26
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(13)
<223> OTHER INFORMATION: n = dabcyl-dt
<220> FEATURE:
<221> NAME/KEY: misc_feature
<222> LOCATION: (15)..(15)
<223> OTHER INFORMATION: n = fluorescein-dt

<400> SEQUENCE: 26
ctatgaactg acnrngacct cactaccaag                                         30

<210> SEQ ID NO 27
<211> LENGTH: 83
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(13)
<223> OTHER INFORMATION: n = dabcyl-dt
<220> FEATURE:
<221> NAME/KEY: misc_feature
<222> LOCATION: (15)..(15)
<223> OTHER INFORMATION: n = fluorescein-dt

<400> SEQUENCE: 27
ctatgaactg acnrngacct cactaccaag atgccatcga tggtctttgg tatgtgggt         60 ccgagggtag agctctgaac tcg                                                83

<210> SEQ ID NO 28
<211> LENGTH: 46
<212> TYPE: DNA
<213> ORGANISM: Artificial Sequence
```

<220> FEATURE:
<223> OTHER INFORMATION: Synthetic construct

<400> SEQUENCE: 28
ccccggtaac ggctagatgg gtattggtta gtgtgggccc gtgttg            46

<210> SEQ ID NO 29
<211> LENGTH: 47
<212> TYPE: DNA
<213> ORGANISM: Artificial Sequence
<220> FEATURE:
<223> OTHER INFORMATION: Synthetic construct

<400> SEQUENCE: 29
ccagggtaag gtataacaat ggtagacagg tgtgtggtcc gggtgct           47

<210> SEQ ID NO 30
<211> LENGTH: 47
<212> TYPE: DNA
<213> ORGANISM: Artificial Sequence
<220> FEATURE:
<223> OTHER INFORMATION: Synthetic construct

<400> SEQUENCE: 30
acacggagca ggtggagttg catctggata gggggtcgcc gggtata          47

<210> SEQ ID NO 31
<211> LENGTH: 48
<212> TYPE: DNA
<213> ORGANISM: Artificial Sequence
<220> FEATURE:
<223> OTHER INFORMATION: Synthetic construct

<400> SEQUENCE: 31
accccaggtc gtttgaagta cctcttggga atgtggtcac cgatgttg          48

<210> SEQ ID NO 32
<211> LENGTH: 47
<212> TYPE: DNA
<213> ORGANISM: Artificial Sequence
<220> FEATURE:
<223> OTHER INFORMATION: Synthetic construct

<400> SEQUENCE: 32
cccaagtacg gttgcgcatg gtaaatatgt ggtgtggtcc cgatgta          47

<210> SEQ ID NO 33
<211> LENGTH: 47
<212> TYPE: DNA
<213> ORGANISM: Artificial Sequence
<220> FEATURE:
<223> OTHER INFORMATION: Synthetic construct

<400> SEQUENCE: 33
cacaggattg cgtggattct tcataatggt ggtgaggtcg agggttg          47

<210> SEQ ID NO 34
<211> LENGTH: 48
<212> TYPE: DNA
<213> ORGANISM: Artificial Sequence
<220> FEATURE:
<223> OTHER INFORMATION: Synthetic construct

<400> SEQUENCE: 34
ccgacaggga ctggttgcca cgggagctgt gtaagagggc cgtgttat         48

<210> SEQ ID NO 35
<211> LENGTH: 48
<212> TYPE: DNA
<213> ORGANISM: Artificial Sequence
<220> FEATURE:
<223> OTHER INFORMATION: Synthetic construct

<400> SEQUENCE: 35
caacggaaag gtggtcgatt tctaggacta ttgaggtcat ccgtggtg                48

<210> SEQ ID NO 36
<211> LENGTH: 47
<212> TYPE: DNA
<213> ORGANISM: Artificial Sequence
<220> FEATURE:
<223> OTHER INFORMATION: Synthetic construct

<400> SEQUENCE: 36
cacccggtta gacggaagtg ggctattgtg tattgggtcg cgatgag                 47

<210> SEQ ID NO 37
<211> LENGTH: 16
<212> TYPE: DNA
<213> ORGANISM: Artificial Sequence
<220> FEATURE:
<223> OTHER INFORMATION: Synthetic construct

<400> SEQUENCE: 37
atgccatcct accaac                                                   16

<210> SEQ ID NO 38
<211> LENGTH: 15
<212> TYPE: DNA
<213> ORGANISM: Artificial Sequence
<220> FEATURE:
<223> OTHER INFORMATION: Synthetic construct

<400> SEQUENCE: 38
tgccatccta ccaac                                                    15

<210> SEQ ID NO 39
<211> LENGTH: 14
<212> TYPE: DNA
<213> ORGANISM: Artificial Sequence
<220> FEATURE:
<223> OTHER INFORMATION: Synthetic construct

<400> SEQUENCE: 39
gccatcctac caac                                                     14

<210> SEQ ID NO 40
<211> LENGTH: 13
<212> TYPE: DNA
<213> ORGANISM: Artificial Sequence
<220> FEATURE:
<223> OTHER INFORMATION: Synthetic construct

<400> SEQUENCE: 40
ccatcctacc aac                                                      13

<210> SEQ ID NO 41
<211> LENGTH: 12
<212> TYPE: DNA
<213> ORGANISM: Artificial Sequence
<220> FEATURE:
<223> OTHER INFORMATION: Synthetic construct

```
<400> SEQUENCE: 41
catcctacca ac                                                          12

<210> SEQ ID NO 42
<211> LENGTH: 11
<212> TYPE: DNA
<213> ORGANISM: Artificial Sequence
<220> FEATURE:
<223> OTHER INFORMATION: Synthetic construct

<400> SEQUENCE: 42
atcctaccaa c                                                           11

<210> SEQ ID NO 43
<211> LENGTH: 10
<212> TYPE: DNA
<213> ORGANISM: Artificial Sequence
<220> FEATURE:
<223> OTHER INFORMATION: Synthetic construct

<400> SEQUENCE: 43
tcctaccaac                                                             10

<210> SEQ ID NO 44
<211> LENGTH: 9
<212> TYPE: DNA
<213> ORGANISM: Artificial Sequence
<220> FEATURE:
<223> OTHER INFORMATION: Synthetic construct

<400> SEQUENCE: 44 cctaccaac                                                               9

<210> SEQ ID NO 45
<211> LENGTH: 8
<212> TYPE: DNA
<213> ORGANISM: Artificial Sequence
<220> FEATURE:
<223> OTHER INFORMATION: Synthetic construct

<400> SEQUENCE: 45 ctaccaac                                                                8

<210> SEQ ID NO 46
<211> LENGTH: 7
<212> TYPE: DNA
<213> ORGANISM: Artificial Sequence
<220> FEATURE:
<223> OTHER INFORMATION: Synthetic construct

<400> SEQUENCE: 46 taccaac                                                                 7

<210> SEQ ID NO 47
<211> LENGTH: 6
<212> TYPE: DNA
<213> ORGANISM: Artificial Sequence
<220> FEATURE:
<223> OTHER INFORMATION: Synthetic construct

<400> SEQUENCE: 47 accaac                                                                  6

<210> SEQ ID NO 48
```

```
<211> LENGTH: 5
<212> TYPE: DNA
<213> ORGANISM: Artificial Sequence
<220> FEATURE:
<223> OTHER INFORMATION: Synthetic construct

<400> SEQUENCE: 48 ccaac                                                                        5

<210> SEQ ID NO 49
<211> LENGTH: 4
<212> TYPE: DNA
<213> ORGANISM: Artificial Sequence
<220> FEATURE:
<223> OTHER INFORMATION: Synthetic construct

<400> SEQUENCE: 49 caac                                                                         4

<210> SEQ ID NO 50
<211> LENGTH: 3
<212> TYPE: DNA
<213> ORGANISM: Artificial Sequence
<220> FEATURE:
<223> OTHER INFORMATION: Synthetic Construct

<400> SEQUENCE: 50 aac                                                                          3

<210> SEQ ID NO 51
<211> LENGTH: 2
<212> TYPE: DNA
<213> ORGANISM: Artificial Sequence
<220> FEATURE:
<223> OTHER INFORMATION: Synthetic construct

<400> SEQUENCE: 51 ac                                                                           2

<210> SEQ ID NO 52
<211> LENGTH: 1
<212> TYPE: DNA
<213> ORGANISM: Artificial Sequence
<220> FEATURE:
<223> OTHER INFORMATION: Synthetic construct

<400> SEQUENCE: 52 c                                                                            1

<210> SEQ ID NO 53
<211> LENGTH: 14
<212> TYPE: DNA
<213> ORGANISM: Artificial Sequence
<220> FEATURE:
<223> OTHER INFORMATION: Synthetic construct

<400> SEQUENCE: 53
gagctctgaa ctcg                                                             14

<210> SEQ ID NO 54
<211> LENGTH: 13
<212> TYPE: DNA
<213> ORGANISM: Artificial Sequence
<220> FEATURE:
<223> OTHER INFORMATION: Synthetic construct

<400> SEQUENCE: 54
```

```
gagctctgaa ctc                                                    13

<210> SEQ ID NO 55
<211> LENGTH: 12
<212> TYPE: DNA
<213> ORGANISM: Artificial Sequence
<220> FEATURE:
<223> OTHER INFORMATION: Synthetic construct

<400> SEQUENCE: 55
gagctctgaa ct                                                     12

<210> SEQ ID NO 56
<211> LENGTH: 11
<212> TYPE: DNA
<213> ORGANISM: Artificial Sequence
<220> FEATURE:
<223> OTHER INFORMATION: Synthetic construct

<400> SEQUENCE: 56
gagctctgaa c                                                      11

<210> SEQ ID NO 57
<211> LENGTH: 10
<212> TYPE: DNA
<213> ORGANISM: Artificial Sequence
<220> FEATURE:
<223> OTHER INFORMATION: Synthetic construct

<400> SEQUENCE: 57
gagctctgaa                                                        10

<210> SEQ ID NO 58
<211> LENGTH: 9
<212> TYPE: DNA
<213> ORGANISM: Artificial Sequence
<220> FEATURE:
<223> OTHER INFORMATION: Synthetic construct

<400> SEQUENCE: 58 gagctctga                                                          9

<210> SEQ ID NO 59
<211> LENGTH: 8
<212> TYPE: DNA
<213> ORGANISM: Artificial Sequence
<220> FEATURE:
<223> OTHER INFORMATION: Synthetic construct

<400> SEQUENCE: 59 gagctctg                                                           8

<210> SEQ ID NO 60
<211> LENGTH: 7
<212> TYPE: DNA
<213> ORGANISM: Artificial Sequence
<220> FEATURE:
<223> OTHER INFORMATION: Synthetic construct

<400> SEQUENCE: 60 gagctct                                                            7

<210> SEQ ID NO 61
<211> LENGTH: 6
<212> TYPE: DNA
```

```
<213> ORGANISM: Artificial Sequence
<220> FEATURE:
<223> OTHER INFORMATION: Synthetic construct

<400> SEQUENCE: 61 gagctc                                                                     6

<210> SEQ ID NO 62
<211> LENGTH: 5
<212> TYPE: DNA
<213> ORGANISM: Artificial Sequence
<220> FEATURE:
<223> OTHER INFORMATION: Synthetic construct

<400> SEQUENCE: 62 gagct                                                                      5

<210> SEQ ID NO 63
<211> LENGTH: 4
<212> TYPE: DNA
<213> ORGANISM: Artificial Sequence
<220> FEATURE:
<223> OTHER INFORMATION: Synthetic construct

<400> SEQUENCE: 63 gagc                                                                       4

<210> SEQ ID NO 64
<211> LENGTH: 3
<212> TYPE: DNA
<213> ORGANISM: Artificial Sequence
<220> FEATURE:
<223> OTHER INFORMATION: Synthetic construct

<400> SEQUENCE: 64 gag                                                                        3

<210> SEQ ID NO 65
<211> LENGTH: 2
<212> TYPE: DNA
<213> ORGANISM: Artificial Sequence
<220> FEATURE:
<223> OTHER INFORMATION: Synthetic construct

<400> SEQUENCE: 65 ga                                                                         2

<210> SEQ ID NO 66
<211> LENGTH: 1
<212> TYPE: DNA
<213> ORGANISM: Artificial Sequence
<220> FEATURE:
<223> OTHER INFORMATION: Synthetic construct

<400> SEQUENCE: 66 g                                                                          1

<210> SEQ ID NO 67
<211> LENGTH: 12
<212> TYPE: DNA
<213> ORGANISM: Artificial Sequence
<220> FEATURE:
<223> OTHER INFORMATION: Synthetic construct

<400> SEQUENCE: 67
ctatgaactg ac                                                             12
```

```
<210> SEQ ID NO 68
<211> LENGTH: 13
<212> TYPE: DNA
<213> ORGANISM: Artificial Sequence
<220> FEATURE:
<223> OTHER INFORMATION: Synthetic construct

<400> SEQUENCE: 68
gatacttgac tga                                              13

<210> SEQ ID NO 69
<211> LENGTH: 13
<212> TYPE: DNA
<213> ORGANISM: Artificial Sequence
<220> FEATURE:
<223> OTHER INFORMATION: Synthetic construct

<400> SEQUENCE: 69
agtcagttca tag                                              13

<210> SEQ ID NO 70
<211> LENGTH: 12
<212> TYPE: DNA
<213> ORGANISM: Artificial Sequence
<220> FEATURE:
<223> OTHER INFORMATION: Synthetic construct

<400> SEQUENCE: 70
ctatgaactg ac                                               12

<210> SEQ ID NO 71
<211> LENGTH: 14
<212> TYPE: DNA
<213> ORGANISM: Artificial Sequence
<220> FEATURE:
<223> OTHER INFORMATION: Synthetic construct

<400> SEQUENCE: 71 cgagttcag agctc                                             14
```